US007468429B2

(12) United States Patent
Shaw et al.

(10) Patent No.: US 7,468,429 B2
(45) Date of Patent: Dec. 23, 2008

(54) **RECOMBINANT *CANDIDA RUGOSA* LIPASES**

(75) Inventors: Jei-Fu Shaw, Taipei (TW); Guan-Chiun Lee, Taipei (TW); Shye-Jye Tang, Taipei (TW)

(73) Assignee: Academia Sinica, Taipei (TW)

( * ) Notice: Subject to any disclaimer, the term of this patent is extended or adjusted under 35 U.S.C. 154(b) by 34 days.

(21) Appl. No.: 11/349,592

(22) Filed: Feb. 7, 2006

(65) Prior Publication Data
US 2006/0121528 A1 Jun. 8, 2006

Related U.S. Application Data

(62) Division of application No. 09/943,857, filed on Aug. 31, 2001, now Pat. No. 7,052,879.

(51) Int. Cl.
*C07H 21/04* (2006.01)
*C12N 9/16* (2006.01)
*C12P 21/00* (2006.01)
(52) U.S. Cl. ................... 536/23.1; 435/196; 435/71.1
(58) Field of Classification Search .................. None
See application file for complete search history.

(56) References Cited

FOREIGN PATENT DOCUMENTS

WO   WO 99/14338   3/1999

OTHER PUBLICATIONS

Longhi et al. Cloning and nucleotide acid sequences of two lipase genes from *Candida cylindracea*. Biochimica et Biophysica Acta 1992, 1131, 227-232.*
Diczfalusy et al, Isolation of carboxylester lipase (CEL) isoenzymes from *Candida rugosa* and identification of the corresponding genes. Arch Biochem Biophys. Dec. 1, 1997;348(1):1-8.*
Longhi et al, Cloning and nucleotide sequences of two lipase genes from *Candida cylindracea*. Biochim Biophys Acta. Jun. 15, 1992;1131(2):227-32.*
Benjamin et al, *Candida rugosa* lipases: molecular biology and versatility in biotechnology. Yeast. Sep. 15,1998;14(12):1069-87. Review.*
Mancheno et al, Structural insights into the lipase/esterase behavior in the *Candida rugosa* lipases family: crystal structure of the lipase 2 isoenzyme at 1.97A resolution. J Mol Biol. Oct. 3, 2003;332(5):1059-69.*

Lilia Alberghina, et al. *Cloning, Sequencing, and Expression of Candida rugosa Lipases*. Methods in Enzymology 284:246-260, 1997. XP002067443.
Stefania Brocca, et al. *Design, Total Synthesis, and functional overexpression of the Candida rugosa lip1 gene coding for a major industrial lipase*. Protein Science 7(6):1415-1422, 1998. XP00929163.
Yoshiyuki Kawaguchi, et al. *The codon CUG is read as serine in an asporogenic yeast Candida cylindracea*. 341(6238):164-166, Sep. 1989. XP000084053.
Shye-Jye Tang, et al. *Recombinant Expression of the Candida rugosa lip4 Lipase in Escherichia coli*. Protein Expression and Purification 20:308-313, 2000. XP002204904.
Guan-Chiun Lee, Shye-Jye Tang, Kuang-Hui Sun, Jei-Fu Shaw. *Analysis of the Gene Family Encoding Lipases in Candida rugosa by Competitive Reverse Transcription-PCR*. Applied and Environmental Microbiology, vol. 65, No. 9, Sep. 1999, pp. 3888-3895.
Shye-Jye Tang, Jei-Fu Shaw, Kuang-Hui Sun, Guang-Huan Sun, Terng-Yuan Chang, Ching-Kai Lin, Yuh-Chih Lo, and Guang-Chiun Lee. *Recombinant Expression and Characterization of the Candida rugosa lip4 Lipase in Pichia pastoris: Comparison of Glycosylation, Activity, and Stability*. Archives of Biochemistry and Biophysics, vol. 387, No. 1, Mar. 2001, pp. 93-98.
Rey-Chang Chang, Shu-Jen Chou, Jei-Fu Shaw. *Multiple forms and functions of Candida rugosa lipase*. Biotechnol. Appl. Biochem. vol. 19, 1994. pp. 93-97.
Liming Ge and Peter Rudolph. *Simultaneous Introduction of Multiple Mutations Using Overlap Extension PCR*. Biotechniques, vol. 22, No. 1, Jan. 1997. pp. 28-30.
Miroslaw Cygler and Joseph D. Schrag. *Structure and conformational flexibility of Candida rugosa lipase*. Biochimica et Biophysica Acta, vol. 1441, 1999. pp. 205-214.
Lilia Alberghina et al. "Protein Engineering of a Fungal Lipase". Engineering with Lipases, Kluwer Academia Publishers, Netherlands, pp. 219-228. XP-002067509.
Marina Lotti et al. "Cloning and Analysis of *Candida cylindracea* lipase sequences". Gene 124(1):45-55, 1993. XP-001084201.
Longhi et al. "Lipase 1 precursor (EC 3.1.1.3) (LIP1)".Database Accession No. P20261—XP-002230351.

* cited by examiner

*Primary Examiner*—Sheridan Swope
(74) *Attorney, Agent, or Firm*—Occhiuti Rohlicek & Tsao LLP

(57) ABSTRACT

The present invention features an isolated nucleic acid that includes a mutant DNA encoding a *Candida rugosa* lipase, wherein the mutant DNA is 80% identical to a wild-type DNA encoding the *Candida rugosa* lipase, and includes at least 12 (e.g., 13, 15, 17, or all) universal serine codons corresponding to CTG codons in the wild-type DNA. Each of the universal serine codons, independently, is TCT, TCC, TCA, TCG, AGT, or AGC. The *Candida rugosa* lipase can be *Candida rugosa* lipase 1, 2, 3, 4, 5, or 8.

11 Claims, No Drawings

SEQUENCE LISTING

<160> NUMBER OF SEQ ID NOS: 11

<210> SEQ ID NO 1
<211> LENGTH: 1641
<212> TYPE: DNA
<213> ORGANISM: Candida rugosa
<220> FEATURE:
<221> NAME/KEY: CDS
<222> LOCATION: (1)...(1641)

<400> SEQUENCE: 1

```
tcg atg aat tca cgt ggc cca gcc ggc cgt ctc gga tcg gta ccc acc      48
Ser Met Asn Ser Arg Gly Pro Ala Gly Arg Leu Gly Ser Val Pro Thr
 1               5                  10                  15 gcc acg ctc gcc aac ggc gac acc atc acc ggt ctc aac gcc att gtc      96
Ala Thr Leu Ala Asn Gly Asp Thr Ile Thr Gly Leu Asn Ala Ile Val
             20                  25                  30 aac gaa aag ttt ctc ggc ata ccg ttt gcc gag ccg ccc gtg ggc agc     144
Asn Glu Lys Phe Leu Gly Ile Pro Phe Ala Glu Pro Pro Val Gly Ser
         35                  40                  45 ctc cgc ttc aag ccg ccc gtg ccg tac tcg gcg tcg ctc aac ggc cag     192
Leu Arg Phe Lys Pro Pro Val Pro Tyr Ser Ala Ser Leu Asn Gly Gln
     50                  55                  60 cag ttt acc tct tac ggc ccg tct tgc atg cag atg aac cct atg ggc     240
Gln Phe Thr Ser Tyr Gly Pro Ser Cys Met Gln Met Asn Pro Met Gly
 65                  70                  75                  80 tcg ttt gag gac aca ctt ccc aag aat gcg ctt gac ttg gtg ctc cag     288
Ser Phe Glu Asp Thr Leu Pro Lys Asn Ala Leu Asp Leu Val Leu Gln
                 85                  90                  95 tcc aag atc ttc caa gtg gtg ctt ccc aac gac gag gac tgt ctc acc     336
Ser Lys Ile Phe Gln Val Val Leu Pro Asn Asp Glu Asp Cys Leu Thr
            100                 105                 110 atc aac gtg atc cgg ccg ccc ggc acc agg gcc agt gct ggt ctc ccg     384
Ile Asn Val Ile Arg Pro Pro Gly Thr Arg Ala Ser Ala Gly Leu Pro
        115                 120                 125 gtg atg ctc tgg atc ttt ggc ggt ggg ttt gag ctt ggc ggc tcc agc     432
Val Met Leu Trp Ile Phe Gly Gly Gly Phe Glu Leu Gly Gly Ser Ser
    130                 135                 140 ctc ttt cca gga gac cag atg gtg gcc aag agc gtg ctc atg ggt aaa     480
Leu Phe Pro Gly Asp Gln Met Val Ala Lys Ser Val Leu Met Gly Lys
145                 150                 155                 160 ccg gtg atc cac gtg agc atg aac tac cgc gtg gcg tca tgg ggg ttc     528
Pro Val Ile His Val Ser Met Asn Tyr Arg Val Ala Ser Trp Gly Phe
```

-continued

```
                165                 170                 175
ttg gcc ggc ccc gac atc cag aac gaa ggc agc ggg aac gcc ggc ttg      576
Leu Ala Gly Pro Asp Ile Gln Asn Glu Gly Ser Gly Asn Ala Gly Leu
            180                 185                 190 cat gac cag cgc ttg gcc atg cag tgg gtg gcg gac aac att gct ggg      624
His Asp Gln Arg Leu Ala Met Gln Trp Val Ala Asp Asn Ile Ala Gly
        195                 200                 205 ttt ggc ggc gac ccg agc aag gtg acc ata tac ggc gag tct gcg ggc      672
Phe Gly Gly Asp Pro Ser Lys Val Thr Ile Tyr Gly Glu Ser Ala Gly
    210                 215                 220 agc atg tcg acg ttt gtg cac ctt gtg tgg aac gac ggc gac aac acg      720
Ser Met Ser Thr Phe Val His Leu Val Trp Asn Asp Gly Asp Asn Thr
225                 230                 235                 240 tac aac ggc aag ccg ttg ttc cgc gcc gcc atc atg cag tct ggc tgc      768
Tyr Asn Gly Lys Pro Leu Phe Arg Ala Ala Ile Met Gln Ser Gly Cys
                245                 250                 255 atg gtg ccg tct gac ccg gtg gac ggc acg tac ggc acc gag atc tac      816
Met Val Pro Ser Asp Pro Val Asp Gly Thr Tyr Gly Thr Glu Ile Tyr
            260                 265                 270 aac cag gtg gtg gcg tct gcc ggg tgt ggc agt gcc agc gac aag ctc      864
Asn Gln Val Val Ala Ser Ala Gly Cys Gly Ser Ala Ser Asp Lys Leu
        275                 280                 285 gcg tgc ttg cgc ggc ctt tct cag gac acg ttg tac cag gcc acg agc      912
Ala Cys Leu Arg Gly Leu Ser Gln Asp Thr Leu Tyr Gln Ala Thr Ser
    290                 295                 300 gac acg ccc ggc gtg ttg gcg tac ccg tcg ttg cgg ttg tct tat ctc      960
Asp Thr Pro Gly Val Leu Ala Tyr Pro Ser Leu Arg Leu Ser Tyr Leu
305                 310                 315                 320 ccg cgg ccc gac ggc acc ttc atc acc gac gac atg tat gcc ttg gtg     1008
Pro Arg Pro Asp Gly Thr Phe Ile Thr Asp Asp Met Tyr Ala Leu Val
                325                 330                 335 cgg gac ggc aag tac gca cac gtg ccg gtg atc atc ggc gac cag aac     1056
Arg Asp Gly Lys Tyr Ala His Val Pro Val Ile Ile Gly Asp Gln Asn
            340                 345                 350 gac gag ggc act ttg ttt ggg ctc tct tct ttg aac gtg acc aca gat     1104
Asp Glu Gly Thr Leu Phe Gly Leu Ser Ser Leu Asn Val Thr Thr Asp
        355                 360                 365 gct cag gca cgg gcg tac ttc aag cag tct ttc atc cac gcc agc gat     1152
Ala Gln Ala Arg Ala Tyr Phe Lys Gln Ser Phe Ile His Ala Ser Asp
    370                 375                 380 gcg gag atc gac acg ttg atg gcg gcg tac acc agc gac atc acc cag     1200
Ala Glu Ile Asp Thr Leu Met Ala Ala Tyr Thr Ser Asp Ile Thr Gln
385                 390                 395                 400 ggt tct ccg ttc gac acc ggc atc ttc aat gcc atc acc ccg cag ttc     1248
Gly Ser Pro Phe Asp Thr Gly Ile Phe Asn Ala Ile Thr Pro Gln Phe
                405                 410                 415 aaa cgg atc tct gcg ttg ctt ggc gac ctt gcg ttc acg ctt gcg cgt     1296
Lys Arg Ile Ser Ala Leu Leu Gly Asp Leu Ala Phe Thr Leu Ala Arg
            420                 425                 430 cgc tac ttc ctc aac tac tac cag ggc ggc acc aag tac tcg ttc ctc     1344
Arg Tyr Phe Leu Asn Tyr Tyr Gln Gly Gly Thr Lys Tyr Ser Phe Leu
        435                 440                 445 tct aag cag ctt tct ggg ttg ccc gtc ttg ggc acc ttc cac ggc aac     1392
Ser Lys Gln Leu Ser Gly Leu Pro Val Leu Gly Thr Phe His Gly Asn
    450                 455                 460 gac atc atc tgg cag gac tac ttg gtg ggc agc ggc agt gtg atc tac     1440
Asp Ile Ile Trp Gln Asp Tyr Leu Val Gly Ser Gly Ser Val Ile Tyr
465                 470                 475                 480 aac aac gcg ttc att gcg ttt gcc aac gac ctc gac ccg aac aag gcg     1488
```

```
Asn Asn Ala Phe Ile Ala Phe Ala Asn Asp Leu Asp Pro Asn Lys Ala
            485                 490                 495 ggc ttg tgg acc aac tgg ccc acg tac acc agc agc tct cag tct ggc      1536
Gly Leu Trp Thr Asn Trp Pro Thr Tyr Thr Ser Ser Ser Gln Ser Gly
        500                 505                 510 aac aac ttg atg cag atc aac ggc ttg ggg ttg tac acc ggc aag gac      1584
Asn Asn Leu Met Gln Ile Asn Gly Leu Gly Leu Tyr Thr Gly Lys Asp
        515                 520                 525 aac ttc cgc ccg gat gcg tac agc gcc ctc ttt tcc aac ccg ccg tct      1632
Asn Phe Arg Pro Asp Ala Tyr Ser Ala Leu Phe Ser Asn Pro Pro Ser
        530                 535                 540 ttc ttt gtg                                                           1641
Phe Phe Val
545

<210> SEQ ID NO 2
<211> LENGTH: 547
<212> TYPE: PRT
<213> ORGANISM: Candida rugosa

<400> SEQUENCE: 2

Ser Met Asn Ser Arg Gly Pro Ala Gly Arg Leu Gly Ser Val Pro Thr
 1                5                  10                  15

Ala Thr Leu Ala Asn Gly Asp Thr Ile Thr Gly Leu Asn Ala Ile Val
            20                  25                  30

Asn Glu Lys Phe Leu Gly Ile Pro Phe Ala Glu Pro Pro Val Gly Ser
        35                  40                  45

Leu Arg Phe Lys Pro Pro Val Pro Tyr Ser Ala Ser Leu Asn Gly Gln
 50                  55                  60

Gln Phe Thr Ser Tyr Gly Pro Ser Cys Met Gln Met Asn Pro Met Gly
 65                 70                  75                  80

Ser Phe Glu Asp Thr Leu Pro Lys Asn Ala Leu Asp Leu Val Leu Gln
                85                  90                  95

Ser Lys Ile Phe Gln Val Val Leu Pro Asn Asp Glu Asp Cys Leu Thr
            100                 105                 110

Ile Asn Val Ile Arg Pro Pro Gly Thr Arg Ala Ser Ala Gly Leu Pro
        115                 120                 125

Val Met Leu Trp Ile Phe Gly Gly Gly Phe Glu Leu Gly Gly Ser Ser
130                 135                 140

Leu Phe Pro Gly Asp Gln Met Val Ala Lys Ser Val Leu Met Gly Lys
145                 150                 155                 160

Pro Val Ile His Val Ser Met Asn Tyr Arg Val Ala Ser Trp Gly Phe
                165                 170                 175

Leu Ala Gly Pro Asp Ile Gln Asn Glu Gly Ser Gly Asn Ala Gly Leu
            180                 185                 190

His Asp Gln Arg Leu Ala Met Gln Trp Val Ala Asp Asn Ile Ala Gly
        195                 200                 205

Phe Gly Gly Asp Pro Ser Lys Val Thr Ile Tyr Gly Glu Ser Ala Gly
    210                 215                 220

Ser Met Ser Thr Phe Val His Leu Val Trp Asn Asp Gly Asp Asn Thr
225                 230                 235                 240

Tyr Asn Gly Lys Pro Leu Phe Arg Ala Ala Ile Met Gln Ser Gly Cys
                245                 250                 255

Met Val Pro Ser Asp Pro Val Asp Gly Thr Tyr Gly Thr Glu Ile Tyr
            260                 265                 270

Asn Gln Val Val Ala Ser Ala Gly Cys Gly Ser Ala Ser Asp Lys Leu
```

-continued

```
                275                 280                 285
Ala Cys Leu Arg Gly Leu Ser Gln Asp Thr Leu Tyr Gln Ala Thr Ser
    290                 295                 300

Asp Thr Pro Gly Val Leu Ala Tyr Pro Ser Leu Arg Leu Ser Tyr Leu
305                 310                 315                 320

Pro Arg Pro Asp Gly Thr Phe Ile Thr Asp Met Tyr Ala Leu Val
                325                 330                 335

Arg Asp Gly Lys Tyr Ala His Val Pro Val Ile Ile Gly Asp Gln Asn
                340                 345                 350

Asp Glu Gly Thr Leu Phe Gly Leu Ser Ser Leu Asn Val Thr Thr Asp
            355                 360                 365

Ala Gln Ala Arg Ala Tyr Phe Lys Gln Ser Phe Ile His Ala Ser Asp
    370                 375                 380

Ala Glu Ile Asp Thr Leu Met Ala Ala Tyr Thr Ser Asp Ile Thr Gln
385                 390                 395                 400

Gly Ser Pro Phe Asp Thr Gly Ile Phe Asn Ala Ile Thr Pro Gln Phe
                405                 410                 415

Lys Arg Ile Ser Ala Leu Leu Gly Asp Leu Ala Phe Thr Leu Ala Arg
            420                 425                 430

Arg Tyr Phe Leu Asn Tyr Tyr Gln Gly Gly Thr Lys Tyr Ser Phe Leu
        435                 440                 445

Ser Lys Gln Leu Ser Gly Leu Pro Val Leu Gly Thr Phe His Gly Asn
    450                 455                 460

Asp Ile Ile Trp Gln Asp Tyr Leu Val Gly Ser Gly Val Ile Tyr
465                 470                 475                 480

Asn Asn Ala Phe Ile Ala Phe Ala Asn Asp Leu Asp Pro Asn Lys Ala
                485                 490                 495

Gly Leu Trp Thr Asn Trp Pro Thr Tyr Thr Ser Ser Gln Ser Gly
            500                 505                 510

Asn Asn Leu Met Gln Ile Asn Gly Leu Gly Leu Tyr Thr Gly Lys Asp
        515                 520                 525

Asn Phe Arg Pro Asp Ala Tyr Ser Ala Leu Phe Ser Asn Pro Pro Ser
    530                 535                 540

Phe Phe Val
545

<210> SEQ ID NO 3
<211> LENGTH: 1641
<212> TYPE: DNA
<213> ORGANISM: Candida rugosa
<220> FEATURE:
<221> NAME/KEY: CDS
<222> LOCATION: (1)...(1641)

<400> SEQUENCE: 3 tcg atg aat tca cgt ggc cca gcc ggc cgt ctc gga tcg gta ccc acc        48
Ser Met Asn Ser Arg Gly Pro Ala Gly Arg Leu Gly Ser Val Pro Thr
 1               5                  10                  15 gcc aag ctc gcc aac ggc gac acc atc acc ggt ctc aac gcc atc atc        96
Ala Lys Leu Ala Asn Gly Asp Thr Ile Thr Gly Leu Asn Ala Ile Ile
                20                  25                  30 aac gag gcg ttc ctc ggc att ccc ttt gcc gag ccg ccg gtg ggc aac       144
Asn Glu Ala Phe Leu Gly Ile Pro Phe Ala Glu Pro Pro Val Gly Asn
            35                  40                  45 ctc cgc ttc aag gac cct gtg ccg tac tct ggc tcg ctc aac ggc cag       192
Leu Arg Phe Lys Asp Pro Val Pro Tyr Ser Gly Ser Leu Asn Gly Gln
        50                  55                  60
```

```
aag ttc act tct tac ggc ccg tct tgc atg cag cag aac ccc gag ggc      240
Lys Phe Thr Ser Tyr Gly Pro Ser Cys Met Gln Gln Asn Pro Glu Gly
 65              70                  75                  80 acg ttt gaa gag aac ctt ggc aag acg gca ctc gac ttg gtg atg cag      288
Thr Phe Glu Glu Asn Leu Gly Lys Thr Ala Leu Asp Leu Val Met Gln
                 85                  90                  95 tcc aag gtg ttc cag gcg gtg ctt ccc cag agt gag gac tgc ctc acc      336
Ser Lys Val Phe Gln Ala Val Leu Pro Gln Ser Glu Asp Cys Leu Thr
            100                 105                 110 atc aac gtg gtg cgg ccg ccg ggc acc aag gcg ggc gcc aac ctc ccg      384
Ile Asn Val Val Arg Pro Pro Gly Thr Lys Ala Gly Ala Asn Leu Pro
        115                 120                 125 gtc atg ctc tgg atc ttt ggc ggt ggg ttt gag atc ggc agc ccc acc      432
Val Met Leu Trp Ile Phe Gly Gly Gly Phe Glu Ile Gly Ser Pro Thr
    130                 135                 140 atc ttc cct ccc gcc cag atg gtc acc aag agt gtg ctc atg ggc aag      480
Ile Phe Pro Pro Ala Gln Met Val Thr Lys Ser Val Leu Met Gly Lys
145                 150                 155                 160 cac atc atc cac gtg gcc gtc aac tac cgt gtt gcc tcg tgg ggg ttc      528
His Ile Ile His Val Ala Val Asn Tyr Arg Val Ala Ser Trp Gly Phe
                165                 170                 175 ttg gct ggt gat gac atc aag gcc gag ggc agc ggg aac gcc ggc ttg      576
Leu Ala Gly Asp Asp Ile Lys Ala Glu Gly Ser Gly Asn Ala Gly Leu
            180                 185                 190 aag gac cag cgt ttg ggc atg cag tgg gtg gca gac aac att gcc ggg      624
Lys Asp Gln Arg Leu Gly Met Gln Trp Val Ala Asp Asn Ile Ala Gly
        195                 200                 205 ttc ggc ggc gac ccg agc aag gtg act atc ttt ggc gag tct gcg ggc      672
Phe Gly Gly Asp Pro Ser Lys Val Thr Ile Phe Gly Glu Ser Ala Gly
    210                 215                 220 agc atg tcc gtg ttg tgc cac ctc atc tgg aac gac ggc gac aac acg      720
Ser Met Ser Val Leu Cys His Leu Ile Trp Asn Asp Gly Asp Asn Thr
225                 230                 235                 240 tac aag ggc aag ccg ttg ttc cgc gcg ggc atc atg cag tct gga gcc      768
Tyr Lys Gly Lys Pro Leu Phe Arg Ala Gly Ile Met Gln Ser Gly Ala
                245                 250                 255 atg gtg ccg tct gac ccg gtg gac ggc acg tac ggc aac gag atc tac      816
Met Val Pro Ser Asp Pro Val Asp Gly Thr Tyr Gly Asn Glu Ile Tyr
            260                 265                 270 gac ctc ttt gtc tcg agt gct ggc tgt ggc agc gcc agc gac aag ctc      864
Asp Leu Phe Val Ser Ser Ala Gly Cys Gly Ser Ala Ser Asp Lys Leu
        275                 280                 285 gcg tgc ttg cgc agt gcg tct agc gac acc ttg ctc gat gcc acc aac      912
Ala Cys Leu Arg Ser Ala Ser Ser Asp Thr Leu Leu Asp Ala Thr Asn
    290                 295                 300 aac act cct ggg ttc ttg gcg tac tcc tcg ttg cgg ttg tct tat ctc      960
Asn Thr Pro Gly Phe Leu Ala Tyr Ser Ser Leu Arg Leu Ser Tyr Leu
305                 310                 315                 320 ccg cgg ccc gac ggc aag aac atc acc gat gac atg tac aag ttg gtg     1008
Pro Arg Pro Asp Gly Lys Asn Ile Thr Asp Asp Met Tyr Lys Leu Val
                325                 330                 335 cgc gac ggc aag tat gca agc gtt ccc gtg atc att ggc gac cag aac     1056
Arg Asp Gly Lys Tyr Ala Ser Val Pro Val Ile Ile Gly Asp Gln Asn
            340                 345                 350 gac gag ggc acc atc ttt ggg ctc tct tct ttg aac gtg acc acg aat     1104
Asp Glu Gly Thr Ile Phe Gly Leu Ser Ser Leu Asn Val Thr Thr Asn
        355                 360                 365 gct cag gcc cgt gct tac ttc aag cag tct ttc atc cac gcc agc gac     1152
Ala Gln Ala Arg Ala Tyr Phe Lys Gln Ser Phe Ile His Ala Ser Asp
```

```
        370                 375                 380
gcg gag atc gac acc ttg atg gcg gcg tac ccc cag gac atc acc cag    1200
Ala Glu Ile Asp Thr Leu Met Ala Ala Tyr Pro Gln Asp Ile Thr Gln
385                 390                 395                 400 ggt tct ccg ttc gac acg ggt gtt ctc aac gcc ctc acc ccg cag ttc    1248
Gly Ser Pro Phe Asp Thr Gly Val Leu Asn Ala Leu Thr Pro Gln Phe
                405                 410                 415 aag aga atc tct gcg gtg ctc ggc gac ctt gca ttc atc cac gcc cgc    1296
Lys Arg Ile Ser Ala Val Leu Gly Asp Leu Ala Phe Ile His Ala Arg
                    420                 425                 430 cgc tac ttc ctc aac cac ttc cag ggc ggc acc aag tac tcg ttc ctc    1344
Arg Tyr Phe Leu Asn His Phe Gln Gly Gly Thr Lys Tyr Ser Phe Leu
                435                 440                 445 tct aag cag ctc tct ggg ttg cca atc atg ggc acc ttc cat gcc aac    1392
Ser Lys Gln Leu Ser Gly Leu Pro Ile Met Gly Thr Phe His Ala Asn
                    450                 455                 460 gac att gtg tgg cag gac tac ttg ttg gga agc ggc agc gtc atc tac    1440
Asp Ile Val Trp Gln Asp Tyr Leu Leu Gly Ser Gly Ser Val Ile Tyr
465                 470                 475                 480 aac aac gcg ttt atc gcg ttc gcc acc gac ttg gac ccc aac acc gcg    1488
Asn Asn Ala Phe Ile Ala Phe Ala Thr Asp Leu Asp Pro Asn Thr Ala
                    485                 490                 495 ggg ttg ttg gtg aac tgg ccc aag tac acc agc agc tct cag tct ggc    1536
Gly Leu Leu Val Asn Trp Pro Lys Tyr Thr Ser Ser Ser Gln Ser Gly
                500                 505                 510 aac aac ttg atg atg atc aac gcc ttg ggc ttg tac acc ggc aag gac    1584
Asn Asn Leu Met Met Ile Asn Ala Leu Gly Leu Tyr Thr Gly Lys Asp
                    515                 520                 525 aac ttc cgc acc gct ggc tac gac gcg ttg atg acc aac ccg tct tct    1632
Asn Phe Arg Thr Ala Gly Tyr Asp Ala Leu Met Thr Asn Pro Ser Ser
530                 535                 540 ttc ttt gtg                                                         1641
Phe Phe Val
545

<210> SEQ ID NO 4
<211> LENGTH: 547
<212> TYPE: PRT
<213> ORGANISM: Candida rugosa

<400> SEQUENCE: 4

Ser Met Asn Ser Arg Gly Pro Ala Gly Arg Leu Gly Ser Val Pro Thr
1               5                   10                  15

Ala Lys Leu Ala Asn Gly Asp Thr Ile Thr Gly Leu Asn Ala Ile Ile
                20                  25                  30

Asn Glu Ala Phe Leu Gly Ile Pro Phe Ala Glu Pro Pro Val Gly Asn
            35                  40                  45

Leu Arg Phe Lys Asp Pro Val Pro Tyr Ser Gly Ser Leu Asn Gly Gln
        50                  55                  60

Lys Phe Thr Ser Tyr Gly Pro Ser Cys Met Gln Gln Asn Pro Glu Gly
65              70                  75                  80

Thr Phe Glu Glu Asn Leu Gly Lys Thr Ala Leu Asp Leu Val Met Gln
                85                  90                  95

Ser Lys Val Phe Gln Ala Val Leu Pro Gln Ser Glu Asp Cys Leu Thr
            100                 105                 110

Ile Asn Val Val Arg Pro Pro Gly Thr Lys Ala Gly Ala Asn Leu Pro
        115                 120                 125

Val Met Leu Trp Ile Phe Gly Gly Gly Phe Glu Ile Gly Ser Pro Thr
```

```
                130                 135                 140
Ile Phe Pro Ala Gln Met Val Thr Lys Ser Val Leu Met Gly Lys
145                 150                 155                 160

His Ile Ile His Val Ala Val Asn Tyr Arg Val Ala Ser Trp Gly Phe
                165                 170                 175

Leu Ala Gly Asp Asp Ile Lys Ala Glu Gly Ser Gly Asn Ala Gly Leu
                180                 185                 190

Lys Asp Gln Arg Leu Gly Met Gln Trp Val Ala Asp Asn Ile Ala Gly
                195                 200                 205

Phe Gly Gly Asp Pro Ser Lys Val Thr Ile Phe Gly Glu Ser Ala Gly
210                 215                 220

Ser Met Ser Val Leu Cys His Leu Ile Trp Asn Asp Gly Asp Asn Thr
225                 230                 235                 240

Tyr Lys Gly Lys Pro Leu Phe Arg Ala Gly Ile Met Gln Ser Gly Ala
                245                 250                 255

Met Val Pro Ser Asp Pro Val Asp Gly Thr Tyr Gly Asn Glu Ile Tyr
                260                 265                 270

Asp Leu Phe Val Ser Ser Ala Gly Cys Gly Ser Ala Ser Asp Lys Leu
                275                 280                 285

Ala Cys Leu Arg Ser Ala Ser Ser Asp Thr Leu Leu Asp Ala Thr Asn
                290                 295                 300

Asn Thr Pro Gly Phe Leu Ala Tyr Ser Ser Leu Arg Leu Ser Tyr Leu
305                 310                 315                 320

Pro Arg Pro Asp Gly Lys Asn Ile Thr Asp Asp Met Tyr Lys Leu Val
                325                 330                 335

Arg Asp Gly Lys Tyr Ala Ser Val Pro Val Ile Ile Gly Asp Gln Asn
                340                 345                 350

Asp Glu Gly Thr Ile Phe Gly Leu Ser Ser Leu Asn Val Thr Thr Asn
                355                 360                 365

Ala Gln Ala Arg Ala Tyr Phe Lys Gln Ser Phe Ile His Ala Ser Asp
                370                 375                 380

Ala Glu Ile Asp Thr Leu Met Ala Ala Tyr Pro Gln Asp Ile Thr Gln
385                 390                 395                 400

Gly Ser Pro Phe Asp Thr Gly Val Leu Asn Ala Leu Thr Pro Gln Phe
                405                 410                 415

Lys Arg Ile Ser Ala Val Leu Gly Asp Leu Ala Phe Ile His Ala Arg
                420                 425                 430

Arg Tyr Phe Leu Asn His Phe Gln Gly Gly Thr Lys Tyr Ser Phe Leu
                435                 440                 445

Ser Lys Gln Leu Ser Gly Leu Pro Ile Met Gly Thr Phe His Ala Asn
450                 455                 460

Asp Ile Val Trp Gln Asp Tyr Leu Leu Gly Ser Gly Ser Val Ile Tyr
465                 470                 475                 480

Asn Asn Ala Phe Ile Ala Phe Ala Thr Asp Leu Asp Pro Asn Thr Ala
                485                 490                 495

Gly Leu Leu Val Asn Trp Pro Lys Tyr Thr Ser Ser Ser Gln Ser Gly
                500                 505                 510

Asn Asn Leu Met Met Ile Asn Ala Leu Gly Leu Tyr Thr Gly Lys Asp
                515                 520                 525

Asn Phe Arg Thr Ala Gly Tyr Asp Ala Leu Met Thr Asn Pro Ser Ser
                530                 535                 540

Phe Phe Val
545
```

```
<210> SEQ ID NO 5
<211> LENGTH: 1641
<212> TYPE: DNA
<213> ORGANISM: Candida rugosa
<220> FEATURE:
<221> NAME/KEY: CDS
<222> LOCATION: (1)...(1641)

<400> SEQUENCE: 5 tcg atg aat tca cgt ggc cca gcc ggc cgt ctc gga tcg gta ccc act         48
Ser Met Asn Ser Arg Gly Pro Ala Gly Arg Leu Gly Ser Val Pro Thr
 1               5                  10                  15 gcc acg ctc gcc aac ggc gac acc atc acc ggt ctc aac gcc atc atc         96
Ala Thr Leu Ala Asn Gly Asp Thr Ile Thr Gly Leu Asn Ala Ile Ile
             20                  25                  30 aac gag gcg ttc ctc ggt att ccc ttt gct cag ccg ccg gtg ggc aac        144
Asn Glu Ala Phe Leu Gly Ile Pro Phe Ala Gln Pro Pro Val Gly Asn
         35                  40                  45 ctc cgc ttc aag ccg cct gtg ccg tac tcg gcg tct ctc aat ggt cag        192
Leu Arg Phe Lys Pro Pro Val Pro Tyr Ser Ala Ser Leu Asn Gly Gln
     50                  55                  60 aag ttt act tcg tat ggc cct tcg tgc atg cag atg aac cca ttg ggc        240
Lys Phe Thr Ser Tyr Gly Pro Ser Cys Met Gln Met Asn Pro Leu Gly
 65                  70                  75                  80 aac tgg gac tcc tcg ctt ccc aag gct gcc atc aac tcc ttg atg cag        288
Asn Trp Asp Ser Ser Leu Pro Lys Ala Ala Ile Asn Ser Leu Met Gln
                 85                  90                  95 tcc aag ctc ttc cag gcg gtg ctt cct aac ggc gag gac tgt ctc acc        336
Ser Lys Leu Phe Gln Ala Val Leu Pro Asn Gly Glu Asp Cys Leu Thr
            100                 105                 110 atc aac gtg gtg cgg ccg tca ggc acc aag ccg ggt gcc aac ctc ccc        384
Ile Asn Val Val Arg Pro Ser Gly Thr Lys Pro Gly Ala Asn Leu Pro
        115                 120                 125 gtg atg gtg tgg att ttt ggc ggc ggg ttt gag gtt ggc ggc tcc agt        432
Val Met Val Trp Ile Phe Gly Gly Gly Phe Glu Val Gly Gly Ser Ser
    130                 135                 140 ctc ttc cct ccc gca cag atg atc acc gcc agc gtg ctt atg ggc aag        480
Leu Phe Pro Pro Ala Gln Met Ile Thr Ala Ser Val Leu Met Gly Lys
145                 150                 155                 160 ccc atc atc cac gtg agc atg aac tac cgc gtt gct tcg tgg ggg ttc        528
Pro Ile Ile His Val Ser Met Asn Tyr Arg Val Ala Ser Trp Gly Phe
                165                 170                 175 ttg gct ggt cca gac atc aag gcc gag ggc agc ggg aac gcc ggt ttg        576
Leu Ala Gly Pro Asp Ile Lys Ala Glu Gly Ser Gly Asn Ala Gly Leu
            180                 185                 190 cac gac caa cgc ttg ggt ttg cag tgg gtg gcg gac aac att gcc ggg        624
His Asp Gln Arg Leu Gly Leu Gln Trp Val Ala Asp Asn Ile Ala Gly
        195                 200                 205 ttc ggc ggc gac ccg tcc aag gtg acc atc ttt ggt gag tcg gcg ggc        672
Phe Gly Gly Asp Pro Ser Lys Val Thr Ile Phe Gly Glu Ser Ala Gly
    210                 215                 220 agc atg tcg gta atg tgt cag ctc ctc tgg aac gac ggc gac aac acg        720
Ser Met Ser Val Met Cys Gln Leu Leu Trp Asn Asp Gly Asp Asn Thr
225                 230                 235                 240 tac aac ggc aag ccg ttg ttc cgt gcc gcc atc atg cag tct ggg gcc        768
Tyr Asn Gly Lys Pro Leu Phe Arg Ala Ala Ile Met Gln Ser Gly Ala
                245                 250                 255 atg gtg ccg tcg gac ccg gtg gat ggg ccc tac ggc acg cag atc tac        816
Met Val Pro Ser Asp Pro Val Asp Gly Pro Tyr Gly Thr Gln Ile Tyr
            260                 265                 270
```

-continued

```
gac cag gtg gtt gct tca gcc ggc tgt ggc agt gcc agc gac aag ctc       864
Asp Gln Val Val Ala Ser Ala Gly Cys Gly Ser Ala Ser Asp Lys Leu
        275                 280                 285 gcg tgc ttg cgc agc atc tcg aac gac aaa ctc ttc cag gcc acc agc       912
Ala Cys Leu Arg Ser Ile Ser Asn Asp Lys Leu Phe Gln Ala Thr Ser
    290                 295                 300 gac act ccg ggg gcc ttg gcg tac ccc tcg ttg cgg ttg tcg ttt ctc       960
Asp Thr Pro Gly Ala Leu Ala Tyr Pro Ser Leu Arg Leu Ser Phe Leu
305                 310                 315                 320 ccg cgg ccc gac ggc acc ttc atc acc gat gac atg ttc aag ttg gtg      1008
Pro Arg Pro Asp Gly Thr Phe Ile Thr Asp Asp Met Phe Lys Leu Val
                325                 330                 335 cgc gac ggc aag tgt gcc aac gtt ccg gtg atc att ggc gac cag aac      1056
Arg Asp Gly Lys Cys Ala Asn Val Pro Val Ile Ile Gly Asp Gln Asn
            340                 345                 350 gac gag ggc aca gtg ttt gcg ttg tcc agc ttg aac gtg act acg gat      1104
Asp Glu Gly Thr Val Phe Ala Leu Ser Ser Leu Asn Val Thr Thr Asp
        355                 360                 365 gct cag gca cgc cag tac ttc aag gaa agc ttc atc cac gcc agc gac      1152
Ala Gln Ala Arg Gln Tyr Phe Lys Glu Ser Phe Ile His Ala Ser Asp
    370                 375                 380 gcg gag atc gac acc ttg atg gcg gcg tac ccc agc gac atc acc cag      1200
Ala Glu Ile Asp Thr Leu Met Ala Ala Tyr Pro Ser Asp Ile Thr Gln
385                 390                 395                 400 ggt agt ccg ttc gac acc ggc atc ttc aac gcc atc acc ccg cag ttc      1248
Gly Ser Pro Phe Asp Thr Gly Ile Phe Asn Ala Ile Thr Pro Gln Phe
                405                 410                 415 aaa cgg att gca gcg gtg ctt ggt gac ctt gcg ttc act ctc ccc cgg      1296
Lys Arg Ile Ala Ala Val Leu Gly Asp Leu Ala Phe Thr Leu Pro Arg
            420                 425                 430 cgc tac ttc ctc aac cac ttc cag ggc ggc acc aag tac tcg ttc ctc      1344
Arg Tyr Phe Leu Asn His Phe Gln Gly Gly Thr Lys Tyr Ser Phe Leu
        435                 440                 445 tcg aag cag ctt agt ggg ttg ccg gtg att ggc acc cac cac gcc aac      1392
Ser Lys Gln Leu Ser Gly Leu Pro Val Ile Gly Thr His His Ala Asn
    450                 455                 460 gac att gtg tgg cag gac ttt ttg gtg agc cac agc agc gcc gtg tac      1440
Asp Ile Val Trp Gln Asp Phe Leu Val Ser His Ser Ser Ala Val Tyr
465                 470                 475                 480 aac aac gcg ttt att gcc ttt gcc aac gac ctc gac ccg aac aag gcc      1488
Asn Asn Ala Phe Ile Ala Phe Ala Asn Asp Leu Asp Pro Asn Lys Ala
                485                 490                 495 ggt ttg ctt gtg aac tgg ccc aag tac acc agc agc tct cag tca ggc      1536
Gly Leu Leu Val Asn Trp Pro Lys Tyr Thr Ser Ser Ser Gln Ser Gly
            500                 505                 510 aac aac ttg ttg cag atc aac gcc ttg ggc ttg tac acc ggc aag gac      1584
Asn Asn Leu Leu Gln Ile Asn Ala Leu Gly Leu Tyr Thr Gly Lys Asp
        515                 520                 525 aac ttc cgc acc gct ggc tac gac gcg ttg ttt acc aac ccg tct tct      1632
Asn Phe Arg Thr Ala Gly Tyr Asp Ala Leu Phe Thr Asn Pro Ser Ser
    530                 535                 540 ttc ttt gtg                                                          1641
Phe Phe Val
545
```

```
<210> SEQ ID NO 6
<211> LENGTH: 547
<212> TYPE: PRT
<213> ORGANISM: Candida rugosa
```

```
<400> SEQUENCE: 6

Ser Met Asn Ser Arg Gly Pro Ala Gly Arg Leu Gly Ser Val Pro Thr
  1               5                  10                  15

Ala Thr Leu Ala Asn Gly Asp Thr Ile Thr Gly Leu Asn Ala Ile Ile
             20                  25                  30

Asn Glu Ala Phe Leu Gly Ile Pro Phe Ala Gln Pro Pro Val Gly Asn
             35                  40                  45

Leu Arg Phe Lys Pro Pro Val Pro Tyr Ser Ala Ser Leu Asn Gly Gln
 50                  55                  60

Lys Phe Thr Ser Tyr Gly Pro Ser Cys Met Gln Met Asn Pro Leu Gly
 65                  70                  75                  80

Asn Trp Asp Ser Leu Pro Lys Ala Ala Ile Asn Ser Leu Met Gln
             85                  90                  95

Ser Lys Leu Phe Gln Ala Val Leu Pro Asn Gly Glu Asp Cys Leu Thr
            100                 105                 110

Ile Asn Val Val Arg Pro Ser Gly Thr Lys Pro Gly Ala Asn Leu Pro
            115                 120                 125

Val Met Val Trp Ile Phe Gly Gly Phe Glu Val Gly Gly Ser Ser
            130                 135                 140

Leu Phe Pro Pro Ala Gln Met Ile Thr Ala Ser Val Leu Met Gly Lys
145                 150                 155                 160

Pro Ile Ile His Val Ser Met Asn Tyr Arg Val Ala Ser Trp Gly Phe
            165                 170                 175

Leu Ala Gly Pro Asp Ile Lys Ala Glu Gly Ser Gly Asn Ala Gly Leu
            180                 185                 190

His Asp Gln Arg Leu Gly Leu Gln Trp Val Ala Asp Asn Ile Ala Gly
            195                 200                 205

Phe Gly Gly Asp Pro Ser Lys Val Thr Ile Phe Gly Glu Ser Ala Gly
            210                 215                 220

Ser Met Ser Val Met Cys Gln Leu Leu Trp Asn Asp Gly Asp Asn Thr
225                 230                 235                 240

Tyr Asn Gly Lys Pro Leu Phe Arg Ala Ala Ile Met Gln Ser Gly Ala
            245                 250                 255

Met Val Pro Ser Asp Pro Val Asp Gly Pro Tyr Gly Thr Gln Ile Tyr
            260                 265                 270

Asp Gln Val Val Ala Ser Ala Gly Cys Gly Ser Ala Ser Asp Lys Leu
            275                 280                 285

Ala Cys Leu Arg Ser Ile Ser Asn Asp Lys Leu Phe Gln Ala Thr Ser
            290                 295                 300

Asp Thr Pro Gly Ala Leu Ala Tyr Pro Ser Leu Arg Leu Ser Phe Leu
305                 310                 315                 320

Pro Arg Pro Asp Gly Thr Phe Ile Thr Asp Asp Met Phe Lys Leu Val
            325                 330                 335

Arg Asp Gly Lys Cys Ala Asn Val Pro Val Ile Ile Gly Asp Gln Asn
            340                 345                 350

Asp Glu Gly Thr Val Phe Ala Leu Ser Ser Leu Asn Val Thr Thr Asp
            355                 360                 365

Ala Gln Ala Arg Gln Tyr Phe Lys Glu Ser Phe Ile His Ala Ser Asp
            370                 375                 380

Ala Glu Ile Asp Thr Leu Met Ala Ala Tyr Pro Ser Asp Ile Thr Gln
385                 390                 395                 400

Gly Ser Pro Phe Asp Thr Gly Ile Phe Asn Ala Ile Thr Pro Gln Phe
            405                 410                 415
```

```
Lys Arg Ile Ala Ala Val Leu Gly Asp Leu Ala Phe Thr Leu Pro Arg
                420                 425                 430

Arg Tyr Phe Leu Asn His Phe Gln Gly Gly Thr Lys Tyr Ser Phe Leu
            435                 440                 445

Ser Lys Gln Leu Ser Gly Leu Pro Val Ile Gly Thr His His Ala Asn
        450                 455                 460

Asp Ile Val Trp Gln Asp Phe Leu Val Ser His Ser Ala Val Tyr
465                 470                 475                 480

Asn Asn Ala Phe Ile Ala Phe Ala Asn Asp Leu Asp Pro Asn Lys Ala
                485                 490                 495

Gly Leu Leu Val Asn Trp Pro Lys Tyr Thr Ser Ser Gln Ser Gly
            500                 505                 510

Asn Asn Leu Leu Gln Ile Asn Ala Leu Gly Leu Tyr Thr Gly Lys Asp
        515                 520                 525

Asn Phe Arg Thr Ala Gly Tyr Asp Ala Leu Phe Thr Asn Pro Ser Ser
530                 535                 540

Phe Phe Val
545

<210> SEQ ID NO 7
<211> LENGTH: 1641
<212> TYPE: DNA
<213> ORGANISM: Candida rugosa
<220> FEATURE:
<221> NAME/KEY: CDS
<222> LOCATION: (1)...(1641)

<400> SEQUENCE: 7 tcg atg aat tca cgt ggc cca gcc ggc cgt ctc gga tcg gta ccc act        48
Ser Met Asn Ser Arg Gly Pro Ala Gly Arg Leu Gly Ser Val Pro Thr
 1               5                  10                  15 gcc acg ctc gcc aac ggc gac acc atc acc ggt ctc aac gcc atc atc        96
Ala Thr Leu Ala Asn Gly Asp Thr Ile Thr Gly Leu Asn Ala Ile Ile
            20                  25                  30 aac gag gcg ttc ctc ggc att ccc ttt gcc gag ccg ccg gtg ggc aac       144
Asn Glu Ala Phe Leu Gly Ile Pro Phe Ala Glu Pro Pro Val Gly Asn
        35                  40                  45 ctc cgc ttc aag gac cct gtg ccg tac cgt ggg tct ctc aac ggt caa       192
Leu Arg Phe Lys Asp Pro Val Pro Tyr Arg Gly Ser Leu Asn Gly Gln
     50                 55                 60 tcc ttc acc gcg tac ggt ccg tct tgc atg cag cag aac ccc gag ggc       240
Ser Phe Thr Ala Tyr Gly Pro Ser Cys Met Gln Gln Asn Pro Glu Gly
 65                 70                  75                  80 acc tac gag gag aac ctc ccc aag gtg gcg ctt gac ttg gtg atg cag       288
Thr Tyr Glu Glu Asn Leu Pro Lys Val Ala Leu Asp Leu Val Met Gln
                85                  90                  95 tcc aag gtg ttc cag gct gtt ctc ccc aac agc gag gac tgc ctc acc       336
Ser Lys Val Phe Gln Ala Val Leu Pro Asn Ser Glu Asp Cys Leu Thr
            100                 105                 110 atc aac gtg gtg cgg ccg ccg ggc acc aag gcg ggc gcc aac ctc ccg       384
Ile Asn Val Val Arg Pro Pro Gly Thr Lys Ala Gly Ala Asn Leu Pro
        115                 120                 125 gtc atg ctc tgg atc ttt ggc ggt ggg ttt gag atc ggc agc ccc acc       432
Val Met Leu Trp Ile Phe Gly Gly Gly Phe Glu Ile Gly Ser Pro Thr
    130                 135                 140 atc ttc cct ccc gct cag atg gtc tcc aag agt gtg ctc atg ggc gag       480
Ile Phe Pro Pro Ala Gln Met Val Ser Lys Ser Val Leu Met Gly Glu
145                 150                 155                 160
```

```
ccc atc atc cac gtg gcc gtc aac tac cgc ttg gcg tcc ttt ggt ttc    528
Pro Ile Ile His Val Ala Val Asn Tyr Arg Leu Ala Ser Phe Gly Phe
            165                 170                 175 ttg gcc ggt ccg gac atc aag gcc gag ggc agc tcc aat gcc ggc ctc    576
Leu Ala Gly Pro Asp Ile Lys Ala Glu Gly Ser Ser Asn Ala Gly Leu
            180                 185                 190 aag gac cag cgc ttg ggc atg cag tgg gtg gca gac aac att gcc ggg    624
Lys Asp Gln Arg Leu Gly Met Gln Trp Val Ala Asp Asn Ile Ala Gly
            195                 200                 205 ttc ggc ggc gac ccg agc aag gtg acc atc ttt ggc gag tct gcg ggc    672
Phe Gly Gly Asp Pro Ser Lys Val Thr Ile Phe Gly Glu Ser Ala Gly
    210                 215                 220 agc atg tcc gtg ttg tgc cac ctt ctc tgg aat ggc ggc gac aac acg    720
Ser Met Ser Val Leu Cys His Leu Leu Trp Asn Gly Gly Asp Asn Thr
225                 230                 235                 240 tac aag ggc aag ccg ttg ttc cgc gcg ggc atc atg cag tct gga gcc    768
Tyr Lys Gly Lys Pro Leu Phe Arg Ala Gly Ile Met Gln Ser Gly Ala
                245                 250                 255 atg gtg ccg tct gac ccg gtg gac ggc acc tat gga gcc caa atc tat    816
Met Val Pro Ser Asp Pro Val Asp Gly Thr Tyr Gly Ala Gln Ile Tyr
            260                 265                 270 gac acg ttg gtg gct tct acg ggc tgc agc agt gcc agc aac aag ctt    864
Asp Thr Leu Val Ala Ser Thr Gly Cys Ser Ser Ala Ser Asn Lys Leu
            275                 280                 285 gcg tgc ttg cgt ggt ctt tct act cag gca ttg ctc gat gcc acc aac    912
Ala Cys Leu Arg Gly Leu Ser Thr Gln Ala Leu Leu Asp Ala Thr Asn
    290                 295                 300 gac acc cct ggg ttc ttg tcg tac acc tcg ttg cgg ttg tct tat ctc    960
Asp Thr Pro Gly Phe Leu Ser Tyr Thr Ser Leu Arg Leu Ser Tyr Leu
305                 310                 315                 320 ccg cgg ccc gac ggc gcc aac atc acc gat gac atg tac aag ttg gta   1008
Pro Arg Pro Asp Gly Ala Asn Ile Thr Asp Asp Met Tyr Lys Leu Val
                325                 330                 335 cgc gac ggc aag tat gca agc gtt ccc gtg atc att ggc gac cag aac   1056
Arg Asp Gly Lys Tyr Ala Ser Val Pro Val Ile Ile Gly Asp Gln Asn
            340                 345                 350 gac gag ggc ttc ttg ttt gat ctc tct tct ttg aac acc acc acc gag   1104
Asp Glu Gly Phe Leu Phe Asp Leu Ser Ser Leu Asn Thr Thr Thr Glu
            355                 360                 365 gcc gac gcc gag gca tac ctc aga aag tct ttc atc cac gcc acc gac   1152
Ala Asp Ala Glu Ala Tyr Leu Arg Lys Ser Phe Ile His Ala Thr Asp
    370                 375                 380 gcc gat atc acc gca ttg aag gcg gcg tac ccc agc gat gtc acc cag   1200
Ala Asp Ile Thr Ala Leu Lys Ala Ala Tyr Pro Ser Asp Val Thr Gln
385                 390                 395                 400 ggt tct ccg ttc gac acg ggc att ctc aac gcc ctt aca ccc cag ctc   1248
Gly Ser Pro Phe Asp Thr Gly Ile Leu Asn Ala Leu Thr Pro Gln Leu
                405                 410                 415 aag cgg atc aat gct gtg ctt ggc gac ctc acc ttt acc ctc tcg cgc   1296
Lys Arg Ile Asn Ala Val Leu Gly Asp Leu Thr Phe Thr Leu Ser Arg
            420                 425                 430 cgc tac ttc ctc aac cac tac acc ggt ggt ccc aag tac tcg ttc ctc   1344
Arg Tyr Phe Leu Asn His Tyr Thr Gly Gly Pro Lys Tyr Ser Phe Leu
            435                 440                 445 tct aag cag ctt tct ggg ttg ccc att ctc ggt acg ttc cac gcg aac   1392
Ser Lys Gln Leu Ser Gly Leu Pro Ile Leu Gly Thr Phe His Ala Asn
    450                 455                 460 gac att gtg tgg cag cac ttt ttg ttg ggc agc ggc agc gtc atc tac   1440
Asp Ile Val Trp Gln His Phe Leu Leu Gly Ser Gly Ser Val Ile Tyr
465                 470                 475                 480
```

```
aac aac gcg ttc atc gcg ttt gcc acc gac ttg gac ccc aac acc gcg    1488
Asn Asn Ala Phe Ile Ala Phe Ala Thr Asp Leu Asp Pro Asn Thr Ala
            485                 490                 495 ggc ttg tct gtg cag tgg ccc aag tac acc agc agc tct cag gcg ggg    1536
Gly Leu Ser Val Gln Trp Pro Lys Tyr Thr Ser Ser Ser Gln Ala Gly
        500                 505                 510 gac aac ttg atg cag atc agt gcc ttg ggc ttg tac acc ggc aag gac    1584
Asp Asn Leu Met Gln Ile Ser Ala Leu Gly Leu Tyr Thr Gly Lys Asp
        515                 520                 525 aac ttc cgc acc gcc ggc tac aac gct ttg ttt gcc gac ccg tct cac    1632
Asn Phe Arg Thr Ala Gly Tyr Asn Ala Leu Phe Ala Asp Pro Ser His
    530                 535                 540 ttt ttc gtg                                                         1641
Phe Phe Val
545

<210> SEQ ID NO 8
<211> LENGTH: 547
<212> TYPE: PRT
<213> ORGANISM: Candida rugosa

<400> SEQUENCE: 8

Ser Met Asn Ser Arg Gly Pro Ala Gly Arg Leu Gly Ser Val Pro Thr
1               5                   10                  15

Ala Thr Leu Ala Asn Gly Asp Thr Ile Thr Gly Leu Asn Ala Ile Ile
            20                  25                  30

Asn Glu Ala Phe Leu Gly Ile Pro Phe Ala Glu Pro Pro Val Gly Asn
        35                  40                  45

Leu Arg Phe Lys Asp Pro Val Pro Tyr Arg Gly Ser Leu Asn Gly Gln
    50                  55                  60

Ser Phe Thr Ala Tyr Gly Pro Ser Cys Met Gln Gln Asn Pro Glu Gly
65                  70                  75                  80

Thr Tyr Glu Glu Asn Leu Pro Lys Val Ala Leu Asp Leu Val Met Gln
                85                  90                  95

Ser Lys Val Phe Gln Ala Val Leu Pro Asn Ser Glu Asp Cys Leu Thr
            100                 105                 110

Ile Asn Val Val Arg Pro Pro Gly Thr Lys Ala Gly Ala Asn Leu Pro
        115                 120                 125

Val Met Leu Trp Ile Phe Gly Gly Gly Phe Glu Ile Gly Ser Pro Thr
    130                 135                 140

Ile Phe Pro Pro Ala Gln Met Val Ser Lys Ser Val Leu Met Gly Glu
145                 150                 155                 160

Pro Ile Ile His Val Ala Val Asn Tyr Arg Leu Ala Ser Phe Gly Phe
                165                 170                 175

Leu Ala Gly Pro Asp Ile Lys Ala Glu Gly Ser Ser Asn Ala Gly Leu
            180                 185                 190

Lys Asp Gln Arg Leu Gly Met Gln Trp Val Ala Asp Asn Ile Ala Gly
        195                 200                 205

Phe Gly Gly Asp Pro Ser Lys Val Thr Ile Phe Gly Glu Ser Ala Gly
    210                 215                 220

Ser Met Ser Val Leu Cys His Leu Leu Trp Asn Gly Asp Asn Thr
225                 230                 235                 240

Tyr Lys Gly Lys Pro Leu Phe Arg Ala Gly Ile Met Gln Ser Gly Ala
                245                 250                 255

Met Val Pro Ser Asp Pro Val Asp Gly Thr Tyr Gly Ala Gln Ile Tyr
            260                 265                 270
```

```
Asp Thr Leu Val Ala Ser Thr Gly Cys Ser Ser Ala Ser Asn Lys Leu
        275                 280                 285

Ala Cys Leu Arg Gly Leu Ser Thr Gln Ala Leu Leu Asp Ala Thr Asn
        290                 295                 300

Asp Thr Pro Gly Phe Leu Ser Tyr Thr Ser Leu Arg Leu Ser Tyr Leu
305                 310                 315                 320

Pro Arg Pro Asp Gly Ala Asn Ile Thr Asp Met Tyr Lys Leu Val
                325                 330                 335

Arg Asp Gly Lys Tyr Ala Ser Val Pro Val Ile Ile Gly Asp Gln Asn
            340                 345                 350

Asp Glu Gly Phe Leu Phe Asp Leu Ser Ser Leu Asn Thr Thr Thr Glu
        355                 360                 365

Ala Asp Ala Glu Ala Tyr Leu Arg Lys Ser Phe Ile His Ala Thr Asp
        370                 375                 380

Ala Asp Ile Thr Ala Leu Lys Ala Ala Tyr Pro Ser Asp Val Thr Gln
385                 390                 395                 400

Gly Ser Pro Phe Asp Thr Gly Ile Leu Asn Ala Leu Thr Pro Gln Leu
                405                 410                 415

Lys Arg Ile Asn Ala Val Leu Gly Asp Leu Thr Phe Thr Leu Ser Arg
            420                 425                 430

Arg Tyr Phe Leu Asn His Tyr Thr Gly Gly Pro Lys Tyr Ser Phe Leu
        435                 440                 445

Ser Lys Gln Leu Ser Gly Leu Pro Ile Leu Gly Thr Phe His Ala Asn
        450                 455                 460

Asp Ile Val Trp Gln His Phe Leu Leu Gly Ser Gly Ser Val Ile Tyr
465                 470                 475                 480

Asn Asn Ala Phe Ile Ala Phe Ala Thr Asp Leu Asp Pro Asn Thr Ala
                485                 490                 495

Gly Leu Ser Val Gln Trp Pro Lys Tyr Thr Ser Ser Gln Ala Gly
            500                 505                 510

Asp Asn Leu Met Gln Ile Ser Ala Leu Gly Leu Tyr Thr Gly Lys Asp
        515                 520                 525

Asn Phe Arg Thr Ala Gly Tyr Asn Ala Leu Phe Ala Asp Pro Ser His
        530                 535                 540

Phe Phe Val
545

<210> SEQ ID NO 9
<211> LENGTH: 1641
<212> TYPE: DNA
<213> ORGANISM: Candida rugosa
<220> FEATURE:
<221> NAME/KEY: CDS
<222> LOCATION: (1)...(1641)

<400> SEQUENCE: 9 tcg atg aat tca cgt ggc cca gcc ggc cgt ctc gga tcg gta ccc act    48
Ser Met Asn Ser Arg Gly Pro Ala Gly Arg Leu Gly Ser Val Pro Thr
1               5                   10                  15 gcc acg ctc gcc aac ggc gac acc atc acc ggt ctc aac gcc atc atc    96
Ala Thr Leu Ala Asn Gly Asp Thr Ile Thr Gly Leu Asn Ala Ile Ile
            20                  25                  30 aac gag gcg ttc ctc ggc att ccc ttt gcc gag ccg ccg gtg ggc aac   144
Asn Glu Ala Phe Leu Gly Ile Pro Phe Ala Glu Pro Pro Val Gly Asn
        35                  40                  45 ctc cgc ttc aag gac ccc gtg ccg tac tcc ggc tcg ctc gat ggc cag   192
Leu Arg Phe Lys Asp Pro Val Pro Tyr Ser Gly Ser Leu Asp Gly Gln
```

-continued

| | | |
|---|---|---|
| Leu Arg Phe Lys Asp Pro Val Pro Tyr Ser Gly Ser Leu Asp Gly Gln<br>     50                   55                   60 | | |
| aag ttc act tct tac ggc ccg tct tgc atg cag cag aac ccc gag ggc<br>Lys Phe Thr Ser Tyr Gly Pro Ser Cys Met Gln Gln Asn Pro Glu Gly<br> 65                   70                   75                 80 | 240 |
| acc tac gag gag aac ctc ccc aag gca gcg ctc gac ttg gtg atg cag<br>Thr Tyr Glu Glu Asn Leu Pro Lys Ala Ala Leu Asp Leu Val Met Gln<br>                   85                   90                 95 | 288 |
| tcc aag gtg ttt gag gcg gtg tct ccg tct agc gag gac tgt ctc acc<br>Ser Lys Val Phe Glu Ala Val Ser Pro Ser Ser Glu Asp Cys Leu Thr<br>                100                105               110 | 336 |
| atc aac gtg gtg cgg ccg ccg ggc acc aag gcg ggt gcc aac ctc ccg<br>Ile Asn Val Val Arg Pro Pro Gly Thr Lys Ala Gly Ala Asn Leu Pro<br>         115                   120               125 | 384 |
| gtg atg ctc tgg atc ttt ggc ggc ggg ttt gag gtg ggt ggc acc agc<br>Val Met Leu Trp Ile Phe Gly Gly Gly Phe Glu Val Gly Gly Thr Ser<br>         130                   135               140 | 432 |
| acc ttc cct ccc gcc cag atg atc acc aag agc att gcc atg ggc aag<br>Thr Phe Pro Pro Ala Gln Met Ile Thr Lys Ser Ile Ala Met Gly Lys<br>145                   150                155               160 | 480 |
| ccc atc atc cac gtg agc gtc aac tac cgc gtg tcg tcg tgg ggg ttc<br>Pro Ile Ile His Val Ser Val Asn Tyr Arg Val Ser Ser Trp Gly Phe<br>                   165                170               175 | 528 |
| ttg gct ggc gac gag atc aag gcc gag ggc agt gcc aac gcc ggt ttg<br>Leu Ala Gly Asp Glu Ile Lys Ala Glu Gly Ser Ala Asn Ala Gly Leu<br>                180                185               190 | 576 |
| aag gac cag cgc atg ggc atg cag tgg gtg gcg gac aac att gcg gcg<br>Lys Asp Gln Arg Met Gly Met Gln Trp Val Ala Asp Asn Ile Ala Ala<br>         195                   200               205 | 624 |
| ttt ggc ggc gac ccg acc aag gtg acc atc ttt ggc gag tct gcg ggc<br>Phe Gly Gly Asp Pro Thr Lys Val Thr Ile Phe Gly Glu Ser Ala Gly<br>         210                   215               220 | 672 |
| agc atg tcg gtc atg tgc cac att ctc tgg aac gac ggc gac aac acg<br>Ser Met Ser Val Met Cys His Ile Leu Trp Asn Asp Gly Asp Asn Thr<br>225                   230                235               240 | 720 |
| tac aag ggc aag ccg ctc ttc cgc gcg ggc atc atg cag tct ggg gcc<br>Tyr Lys Gly Lys Pro Leu Phe Arg Ala Gly Ile Met Gln Ser Gly Ala<br>                   245                250               255 | 768 |
| atg gta ccg tcg gac gcg gtg gac ggc gtc tac ggc aac gag atc ttt<br>Met Val Pro Ser Asp Ala Val Asp Gly Val Tyr Gly Asn Glu Ile Phe<br>                260                265               270 | 816 |
| gac ctc ttg gcg tcg gac gcg ggc tgc ggc agc gcc agc gac aag ctt<br>Asp Leu Leu Ala Ser Asp Ala Gly Cys Gly Ser Ala Ser Asp Lys Leu<br>         275                   280               285 | 864 |
| gcg tgc ttg cgc ggt gtg tct agc gac acg ttg gag gac gcc acc aac<br>Ala Cys Leu Arg Gly Val Ser Ser Asp Thr Leu Glu Asp Ala Thr Asn<br>         290                   295               300 | 912 |
| aac acc cct ggg ttc ttg gcg tac tcc tcg ttg cgg ttg tct tat ctc<br>Asn Thr Pro Gly Phe Leu Ala Tyr Ser Ser Leu Arg Leu Ser Tyr Leu<br>305                   310                315               320 | 960 |
| ccg cgg ccc gac ggc gtg aac atc acc gac gac atg ttt gcc ttg gtc<br>Pro Arg Pro Asp Gly Val Asn Ile Thr Asp Asp Met Phe Ala Leu Val<br>                325                330               335 | 1008 |
| cgc gag ggc aag tat gca agc gtt cct gtg atc atc ggc gac cag aac<br>Arg Glu Gly Lys Tyr Ala Ser Val Pro Val Ile Ile Gly Asp Gln Asn<br>                340                345               350 | 1056 |
| gac gag ggc acc ttc ttt ggc acc tct tct ttg aac gtg acc acg gat<br>Asp Glu Gly Thr Phe Phe Gly Thr Ser Ser Leu Asn Val Thr Thr Asp<br>         355                   360               365 | 1104 |

```
gcc gag gcc cgc cag tac ttc acg cag tct ttt gtc cac gcc agc gac      1152
Ala Glu Ala Arg Gln Tyr Phe Thr Gln Ser Phe Val His Ala Ser Asp
    370                 375                 380 gcg gag ctc gac acg ttg atg acg gcg tac ccc cag gac atc acc cag      1200
Ala Glu Leu Asp Thr Leu Met Thr Ala Tyr Pro Gln Asp Ile Thr Gln
385                 390                 395                 400 ggt tct ccg ttc gac acg ggt gtt ctc aac gcc ctc acc ccg cag ttc      1248
Gly Ser Pro Phe Asp Thr Gly Val Leu Asn Ala Leu Thr Pro Gln Phe
                405                 410                 415 aag aga atc tct gcg gtg ctc ggc gac ctt gcc ttc atc cac gcc cgt      1296
Lys Arg Ile Ser Ala Val Leu Gly Asp Leu Ala Phe Ile His Ala Arg
            420                 425                 430 cgc tac ttc ctc aac cac tac acc ggc ggc acc aag tac tca ttc ctc      1344
Arg Tyr Phe Leu Asn His Tyr Thr Gly Gly Thr Lys Tyr Ser Phe Leu
        435                 440                 445 tct aag cag ctc tct ggc ttg ccg gtg ctc gga acg ttc cac tcc aac      1392
Ser Lys Gln Leu Ser Gly Leu Pro Val Leu Gly Thr Phe His Ser Asn
450                 455                 460 gac att gtc ttc cag gac tac ttg ttg ggc agc ggc tcg ctc atc tac      1440
Asp Ile Val Phe Gln Asp Tyr Leu Leu Gly Ser Gly Ser Leu Ile Tyr
465                 470                 475                 480 aac aac gcg ttc att gcg ttt gcc acg gac ttg gac ccc aac acc gcg      1488
Asn Asn Ala Phe Ile Ala Phe Ala Thr Asp Leu Asp Pro Asn Thr Ala
                485                 490                 495 ggg ttg ttg gtg aag tgg ccc gag tac acc agc agc tct cag tct ggc      1536
Gly Leu Leu Val Lys Trp Pro Glu Tyr Thr Ser Ser Ser Gln Ser Gly
            500                 505                 510 aac aac ttg atg atg atc aac gcc ttg ggc ttg tac acc ggc aag gac      1584
Asn Asn Leu Met Met Ile Asn Ala Leu Gly Leu Tyr Thr Gly Lys Asp
        515                 520                 525 aac tcc cgc acc gcc ggc tac gac gcg ttg ttc tcc aac ccg ccg tct      1632
Asn Ser Arg Thr Ala Gly Tyr Asp Ala Leu Phe Ser Asn Pro Pro Ser
530                 535                 540 ttc ttt gtg                                                          1641
Phe Phe Val
545

<210> SEQ ID NO 10
<211> LENGTH: 547
<212> TYPE: PRT
<213> ORGANISM: Candida rugosa

<400> SEQUENCE: 10

Ser Met Asn Ser Arg Gly Pro Ala Gly Arg Leu Gly Ser Val Pro Thr
 1                5                  10                  15

Ala Thr Leu Ala Asn Gly Asp Thr Ile Thr Gly Leu Asn Ala Ile Ile
             20                  25                  30

Asn Glu Ala Phe Leu Gly Ile Pro Phe Ala Glu Pro Pro Val Gly Asn
         35                  40                  45

Leu Arg Phe Lys Asp Pro Val Pro Tyr Ser Gly Ser Leu Asp Gly Gln
     50                  55                  60

Lys Phe Thr Ser Tyr Gly Pro Ser Cys Met Gln Gln Asn Pro Glu Gly
 65                  70                  75                  80

Thr Tyr Glu Glu Asn Leu Pro Lys Ala Ala Leu Asp Leu Val Met Gln
                 85                  90                  95

Ser Lys Val Phe Glu Ala Val Ser Pro Ser Ser Glu Asp Cys Leu Thr
            100                 105                 110

Ile Asn Val Val Arg Pro Pro Gly Thr Lys Ala Gly Ala Asn Leu Pro
        115                 120                 125
```

-continued

Val Met Leu Trp Ile Phe Gly Gly Phe Glu Val Gly Thr Ser
    130                 135                 140

Thr Phe Pro Pro Ala Gln Met Ile Thr Lys Ser Ile Ala Met Gly Lys
145                 150                 155                 160

Pro Ile Ile His Val Ser Val Asn Tyr Arg Val Ser Trp Gly Phe
                165                 170                 175

Leu Ala Gly Asp Glu Ile Lys Ala Glu Gly Ser Ala Asn Ala Gly Leu
                180                 185                 190

Lys Asp Gln Arg Met Gly Met Gln Trp Val Ala Asp Asn Ile Ala Ala
                195                 200                 205

Phe Gly Gly Asp Pro Thr Lys Val Thr Ile Phe Gly Glu Ser Ala Gly
    210                 215                 220

Ser Met Ser Val Met Cys His Ile Leu Trp Asn Asp Gly Asp Asn Thr
225                 230                 235                 240

Tyr Lys Gly Lys Pro Leu Phe Arg Ala Gly Ile Met Gln Ser Gly Ala
                245                 250                 255

Met Val Pro Ser Asp Ala Val Asp Gly Val Tyr Gly Asn Glu Ile Phe
            260                 265                 270

Asp Leu Leu Ala Ser Asp Ala Gly Cys Gly Ser Ala Ser Asp Lys Leu
        275                 280                 285

Ala Cys Leu Arg Gly Val Ser Ser Asp Thr Leu Glu Asp Ala Thr Asn
    290                 295                 300

Asn Thr Pro Gly Phe Leu Ala Tyr Ser Ser Leu Arg Leu Ser Tyr Leu
305                 310                 315                 320

Pro Arg Pro Asp Gly Val Asn Ile Thr Asp Asp Met Phe Ala Leu Val
                325                 330                 335

Arg Glu Gly Lys Tyr Ala Ser Val Pro Val Ile Ile Gly Asp Gln Asn
                340                 345                 350

Asp Glu Gly Thr Phe Phe Gly Thr Ser Ser Leu Asn Val Thr Thr Asp
            355                 360                 365

Ala Glu Ala Arg Gln Tyr Phe Thr Gln Ser Phe Val His Ala Ser Asp
    370                 375                 380

Ala Glu Leu Asp Thr Leu Met Thr Ala Tyr Pro Gln Asp Ile Thr Gln
385                 390                 395                 400

Gly Ser Pro Phe Asp Thr Gly Val Leu Asn Ala Leu Thr Pro Gln Phe
                405                 410                 415

Lys Arg Ile Ser Ala Val Leu Gly Asp Leu Ala Phe Ile His Ala Arg
                420                 425                 430

Arg Tyr Phe Leu Asn His Tyr Thr Gly Gly Thr Lys Tyr Ser Phe Leu
            435                 440                 445

Ser Lys Gln Leu Ser Gly Leu Pro Val Leu Gly Thr Phe His Ser Asn
    450                 455                 460

Asp Ile Val Phe Gln Asp Tyr Leu Leu Gly Ser Gly Ser Leu Ile Tyr
465                 470                 475                 480

Asn Asn Ala Phe Ile Ala Phe Ala Thr Asp Leu Asp Pro Asn Thr Ala
                485                 490                 495

Gly Leu Leu Val Lys Trp Pro Glu Tyr Thr Ser Ser Gln Ser Gly
                500                 505                 510

Asn Asn Leu Met Met Ile Asn Ala Leu Gly Leu Tyr Thr Gly Lys Asp
            515                 520                 525

Asn Ser Arg Thr Ala Gly Tyr Asp Ala Leu Phe Ser Asn Pro Pro Ser
    530                 535                 540

```
Phe Phe Val
545

<210> SEQ ID NO 11
<211> LENGTH: 13
<212> TYPE: PRT
<213> ORGANISM: Candida rugosa

<400> SEQUENCE: 11

Ser Met Asn Ser Arg Gly Pro Ala Gly Arg Leu Gly Ser
1               5                   10
```

RECOMBINANT *CANDIDA RUGOSA* LIPASES

RELATED APPLICATIONS

This application is a divisional application claiming priority to U.S. application Ser. No. 09/943,857, filed Aug. 31, 2001, now U.S. Pat. No. 7,052,879, the contents of which are incorporated herein in their entirety.

BACKGROUND

Lipase (EC 3.1.1.3) is able to catalyze a wide range of chemical reactions, which include nonspecific and stereospecific hydrolysis, esterfication, trans-esterification, and interesterification. In addition, it catalyzes the hydrolysis of an ester bond at water-lipid interface. See, e.g., Ader et al. (1997) *Methods Enzymol.* 286: 351-385; Gandhi (1997) *J Am Oil Chem. Soc.* 74: 621-634; Klibanov (1990) *Acc. Chem. Res.* 23: 114-120; Shaw et al. (1990) *Biotechnol. Bioeng.* 35:132-137; and Wang et al. (1988) *Biotechnol. Bioeng.* 31: 628-633.

Due to its catalytic abilities, a *Candida rugosa* lipase, among commercial lipases, is widely used in bioindustries. Generally, crude *C. rugosa* lipases are applied in almost all biocatalytic applications, however, enzymes from various suppliers have been reported to show variations in their catalytic efficiency and stereospecificity. See Barton et al. (1990) *Enzyme Microb. Technol.* 12: 577-583. Several lipase isomers (i.e., isozymes) have been isolated from the crude *C. rugosa* lipase, and the lipase isozymes were shown to be different in catalytic efficiency and specificity. See Shaw et al. (1989) *Biotechnol. Lett.* 11: 779-784; Rúa et al. (1993) *Biochem. Biophysl Acta* 1156: 181-189; Diczfalusy et al. (1997) *Arch. Biochem. Biophys.* 348: 1-8.

To date, five lipase-encoding genomic sequences from *C. rugosa* have been characterized. See, for example, Longhi et al. (1992) *Biochim. Biophy. Acta* 1131: 227-232; and Lotti et al. (1993) *Gene* 124: 45-55. The five lipase-encoding genes (LIP1, 2, 3, 4, and 5) have been isolated from a SacI genomic library of the yeast *C. rugosa* by colony hybridization. The five genes encode for mature proteins of 534 residues with putative signal peptides of 15 (in LIP1, 3, 4, and 5) and 14 (in LIP 2) amino acids in length, respectively. The five deduced amino acid sequences share an overall identity of 66% and similarity of 84%. Due to a high sequence homology among the five deduced amino acid sequences and the differential expression level of the five lipase genes (Lee et al. (1999) *Appl. Environ. Microbiol.* 65: 3888-3895), it is difficult to purify each isozyme directly from the cultures of *C. rugosa* on a preparative scale for industrial applications.

Further, although these isozymes are conserved at a catalytic triad (including amino acids S209, H449, and E341) and at the sites involved in disulfide bonds formation (including amino acids C60, C97 and C268, C277), they differ in N-glycosylation sites, isoelectric points, and some other features in their hydrophobic profiles. In addition, each of the isozymes may account for certain properties, such as catalytic efficiency and specificity. See Chang et al. (1994) *Biotechnol. Appl. Biochem.* 19: 93-97. Accordingly, cloning and functional expression of a *C. rugosa* lipase isozyme are desirable for producing a pure isozyme with certain properties for industrial applications.

However, *C. rugosa* is a dimorphic yeast in which the triplet CTG a universal codon for leucine, is read as serine. As a result, the functional expression of a *C. rugosa* isozyme becomes unfeasible in a common host cell (in which CTG is read as leucine). See Kawaguchi et al. (1989) *Nature* 341: 164-166.

SUMMARY

This invention relates to a nucleic acid that can be used to functionally express a heterologous *C. rugosa* lipase in a common host cell.

In one aspect, the present invention features an isolated nucleic acid that includes a mutant DNA encoding a *C. rugosa* lipase. The mutant DNA is at least 80% (e.g., at least 85%, 90%, or 95%) identical to a wild-type DNA encoding the *C. rugosa* lipase, and includes at least 12 (e.g., 13, 15, 17, or all) universal serine codons corresponding to CTG codons in the wild-type DNA. Each of the CTG codon is read as serine in *C. rugosa*. Each of the universal serine codons, independently, is TCT, TCC, TCA, TCG, AGT, or AGC. The term "*C. rugosa* lipase" as used herein refers to a pure isozyme, and includes native *C. rugosa* lipases 1, 2, 3, 4, 5, and 8, as well as their variants. Examples of the just-described isolated nucleic acid include, but are not limited to, SEQ ID NOs:1, 3, 5, 7, and 9, the corresponding amino acid sequences of which are SEQ ID NOs:2, 4, 6, 8, and 10, respectively.

The mutant DNA can be a DNA of SEQ ID NO:1, 3, 5, 7, or 9, or a degenerate variant thereof. The degenerate variant refers to any other DNA sequence which encodes, based on universal codons, the same polypeptide as that encoded by the SEQ ID NO:1, 3, 5, 7, or 9. The mutant DNA can also be a DNA encoding a polypeptide sequence that is at least 90% (e.g., 95%, 98% or 100%) identical to the amino acid sequence of SEQ ID NO:2, 4, 6, 8, or 10. Indeed, the polypeptide sequence need not be a full length of the just-described amino acid sequence as long as its intended catalytic ability in the polypeptide has not been completely abolished. For example, a mutant DNA is a functional fragment containing at least 1070 nucleotides (e.g., 1200, or 1500 nucleotides) of the nucleotide sequence of SEQ ID NO:1, 3, 5, 7, or 9; or a sequence encoding a functional fragment of a polypeptide containing the amino acid sequence of SEQ ID NO:2, 4, 6, 8, or 10, wherein the fragment includes at least 350 amino acids (e.g., 400, or 500 amino acids).

The term "isolated nucleic acid" refers to a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. The above-described isolated nucleic acid of this invention can be introduced into and expressed in a microorganism, which is also within the scope of this invention. An example of the microorganism is a bacterium (e.g., *Escherichia coli*) or yeast (e.g., *Pichia pastoris*).

The "percent identity" (or "percent homology") of two amino acid sequences or of two nucleic acids can be determined using the algorithm of Thompson et al. (CLUSTAL W, 1994 *Nucleic Acids Res.* 22: 4673-4680). An amino acid sequence or a nucleotide sequence can also be used as a "query sequence" to perform a search against public databases to, for example, identify related sequences. Such searches can be performed using the algorithm of Karlin and Altschul (1990 *Proc. Nati. Acad. Sd. USA* 87: 2264-2268), modified as in Karlin and Altschul (1993 *Proc. Nati. Acad. Sd. USA* 90: 5873-5877). Such an algorithm is incorporated into the NBLAST and XBLAST programs of Altschul et al. (1990 *J. Mol. Biol.* 215: 403-410). BLAST nucleotide searches are performed with the NBLAST program, score =100, wordlength =12. BLAST protein searches are performed with the XBLAST program, score =50, wordlength =3. Where gaps exist between two sequences, Gapped BLAST is utilized as described in Altschul et al. (1997 *Nucleic Acids Res.* 25: 3389-3402). When utilizing BLAST and Gapped BLAST programs, the default parameters of the respective programs (e.g., XBLAST and NBLAST) are used. See .ncbi.nlm.nih.gov/.

In another aspect, this invention features a method for preparing a mutant DNA encoding a *C. rugosa* lipase. The method includes providing a wild-type DNA encoding a *C. rugosa* lipase; and conducting PCR amplification by mixing the wild-type DNA, a DNA polymerase, a pair of external primers encompassing the entirety of the wild-type DNA, and a number of pairs of internal primers respectively encompassing fragments of the wild-type DNA. An "external primer" is a PCR primer designed to amplify the entirety of a mutant DNA, and an "internal primer" is a PCR primer designed to amplify a fragment of the mutant DNA; a primer can operate both as an external and as an internal primer. Each of the internal primers includes one or more of universal codons and anticodons for serine selected from TCT, TCC, TCA, TCG, AGT, AGC, AGA, GGA, TGA, CGA, ACT, and GCT, in which the universal codons and anitcodons correspond to at least 12 CTG codons in the wild-type DNA. Further, each internal primer overlaps with another internal or external primer in a manner that a mutant DNA encoding the *C. rugosa* lipase is obtained.

In a further aspect, this invention features a chimeric *C. rugosa* lipase including a substrate interacting domain of a first *C. rugosa* lipase and a non-substrate interacting domain (e.g., a carboxylesterase domain) of a second *C. rugosa* lipase. For example, the second *C. rugosa* lipase is a polypeptide of SEQ ID NO:6, and the first *C. rugosa* lipase is a polypeptide of SEQ ID NO:2, 4, 8, or 10.

Also within the scope of this invention is the use of aforementioned nucleic acid for the manufacture of a *C. rugosa* lipase for biocatalytic applications.

Other features, objects, and advantages of the invention will be apparent from the description and from the claims.

DETAILED DESCRIPTION

This invention relates to an isolated nucleic acid that includes a mutant DNA, which is at least 80% identical to a wild-type DNA encoding a *C. rugosa* lipase.

Set forth below are the mutant nucleic acid sequences of *C. rugosa* lipase 2, *C. rugosa* lipase 3, *C. rugosa* lipase 4, *C. rugosa* lipase 5, and *C. rugosa* lipase 8, wherein all the CTG codons corresponding to serine in the wild-type DNA have been substituted with one of the six universal serine codons (i.e., TCT, TCC, TCA, TCG, AGT, or AGC). The mutated nucleotides are represented in black background. Also shown are the encoded amino acid sequences. The introduced N-terminal peptide (i.e., SMNSRGPAGRLGS; SEQ ID NO:11) is underlined. Mutated amino acid residues are rendered in bold.

Mutant *C. rugosa* lipase 2

```
TCGATGAATTCACGTGGCCCAGCCGGCCGTCTCGGATCCGTACCCACGCCACGCTCGCC    60
 S   M   N   S   R   G   P   A   G   R   L   G   S   V   P   T   A   T   L   A     20
AACGGCGACACCATCACCGGTCTCAACGCCATTGTCAACGAAAAGTTTCTCGGCATACCG  120
 N   G   D   T   I   T   G   L   N   A   I   V   N   E   K   F   L   G   I   P     40
TTTGCCGAGCCGCCCGTGGGCAGCCTCCGCTTCAAGCCGCCCGTGCCGTACTCGGCGTCG  180
 F   A   E   P   P   V   G   S   L   R   F   K   P   P   V   P   Y   S   A   S     60
CTCAACGGCCAGCAGTTTACCTCTTACGGCCCGTCTTGCATGCAGATGAACCCTATGGGC  240
 L   N   G   Q   Q   F   T   S   Y   G   P   S   C   M   Q   M   N   P   M   G     80
TCGTTTGAGGACACACTTCCCAAGAATGCGCTTGACTTGGTGCTCCAGTCCAAGATCTTC  300
 S   F   E   D   T   L   P   K   N   A   L   D   L   V   L   Q   S   K   I   F    100
CAAGTGGTGCTTCCCAACGACGAGGACTGTCTCACCATCAACGTGATCCGGCCGCCCGGC  360
 Q   V   V   L   P   N   D   E   D   C   L   T   I   N   V   I   R   P   P   G    120
ACCAGGGCCAGTGCTGGTCTCCCGGTGATGCTCTGGATCTTTGGCGGTGGGTTTGAGCTT  420
 T   R   A   S   A   G   L   P   V   M   L   W   I   F   G   G   G   F   E   L    140
GGCGGCTCCAGCCTCTTTCCAGGAGACCAGATGGTGGCCAAGAGCGTGCTCATGGGTAAA  480
 G   G   S   S   L   F   P   G   D   Q   M   V   A   K   S   V   L   M   G   K    160
CCGGTGATCCACGTGAGCATGAACTACCGCGTGGCCGTCATGGGGGTTCTTGGCCGGCCCC  540
 P   V   I   G   V   S   M   N   Y   R   V   A   S   W   G   F   L   A   C   P    180
GACATCCAGAACGAAGGCAGCGGGAACGCCGGCTTGCATGACCAGCGCTTGGCCATGCAG  600
 D   I   Q   N   E   G   S   G   N   A   G   L   H   D   Q   R   L   A   M   Q    200
TGGGTGGCGGACAACATTGCTGGGTTTGGCGGCGACCCGAGCAAGGTGACCATATACGGC  660
 W   V   A   D   N   I   A   G   F   G   G   D   P   S   K   V   T   I   Y   G    220
GAGTCTGCGGGCAGCATGTCGACGTTTGTGCACCTTGTGTGGAACGACGGCGACAACACG  720
 E   S   A   G   S   M   S   T   F   V   H   L   V   W   N   D   G   D   N   T    240
TACAACGGCAAGCCGTTGTTCCGCGCCGCCATCATGCAGTCTGGCTGCATGGTGCCGTCT  780
 Y   N   G   K   P   L   F   R   A   A   I   M   Q   S   G   C   M   V   P   S    260
GACCCGGTGGACGGCACGTACGGCACCGAGATCTACAACCAGGTGGTGGCGTCTGCCGGG  840
 D   P   V   D   G   T   Y   G   T   E   I   Y   N   Q   V   V   A   S   A   G    280
TGTGGCAGTGCCAGCGACAAGCTCGCGTGCTTGCGCGGCCTTTCTCAGGACACGTTGTAC  900
 C   G   S   A   S   D   K   L   A   C   L   R   G   L   S   Q   D   T   L   Y    300
CAGGCCACGAGCGACACGCCCGGCGTGTTGGCGTACCCGTCGTTGCGGTTGTCTTATCTC  960
```

-continued

```
           Q  A  T  S  D  T  P  G  V  L  A  Y  P  S  L  R  L  S  Y  L        320
      CCGCGGCCCGACGGCACCTTCATCACCGACGACATGTATGCCTTGGTGCGGGACGGCAAG           1020
           P  R  P  D  G  T  F  I  T  D  D  M  Y  A  L  V  R  D  G  K        340
      TACGCACACGTGCCGGTGATCATCGGCGACCAGAACGACGAGGGCACTTTGTTTGGGCTC           1080
           Y  A  H  V  P  V  I  I  G  D  Q  N  D  E  G  T  L  F  G  L        360
      TCTTCTTTGAACGTGACCACAGATGCTCAGGCACGGGCGTACTTCAAGCAGTCTTTCATC           1140
           S  S  L  N  V  T  T  D  A  Q  A  R  A  Y  F  K  Q  S  F  I        380
      CACGCCAGCGATGCGGAGATCGACACGTTGATGGCGGCGTACACCAGCGACATCACCCAG           1200
           H  A  S  D  A  E  I  D  T  L  M  A  A  Y  T  S  D  I  T  Q        400
      GGTTCTCCGTTCGACACCGGCATCTTCAATGCCATCACCCCGCAGTTCAAACGGATCTCT           1260
           G  S  P  F  D  T  G  I  F  N  A  I  T  P  Q  F  K  R  I  S        420
      GCGTTGCTTGGCGACCTTGCGTTCACGCTTGCGCGTCGCTACTTCCTCAACTACTACCAG           1320
           A  L  L  G  D  L  A  F  T  L  A  R  R  Y  F  L  N  Y  Y  Q        440
      GGCGGCACCAAGTACTCGTTCCTCTCTAAGCAGCTTTCTGGGTTGCCCGTCTTGGGCACC           1380
           G  G  T  K  Y  S  F  L  S  K  Q  L  S  G  L  P  V  L  G  T        460
      TTCCACGGCAACGACATCATCTGGCAGGACTACTTGGTGGGCAGCGGCAGTGTGATCTAC           1440
           F  H  G  N  D  I  I  W  Q  D  Y  L  V  G  S  G  S  V  I  Y        480
      AACAACGCGTTCATTGCGTTTGCCAACGACCTCGACCCGAACAAGGCGGGCTTGTGGACC           1500
           N  N  A  F  I  A  F  A  N  D  L  D  P  N  K  A  G  L  W  T        500
      AACTGGCCCACGTACACCAGCAGCTCTCAGTCTGGCAACAACTTGATGCAGATCAACGGC           1560
           N  W  P  T  Y  T  S  S  S  Q  S  G  N  N  L  M  Q  I  N  G        520
      TTGGGGTTGTACACCGGCAAGGACAACTTCCGCCCGGATGCGTACAGCGCCCTCTTTTCC           1620
           L  G  L  Y  T  G  K  D  N  F  R  P  D  A  Y  S  A  L  F  S        540
      AACCCGCCGTCTTTCTTTGTG                     (SEQ ID NO:1)                 1641
           N  P  P  S  F  F  V                  (SEQ ID NO:2)                 547
```

Mutant *C. rugosa* lipase 3

```
      TCGATGAATTCACGTGGCCCAGCCGGCCGTCTCGGATCGGTACCCACCGCCAAGCTCGCC             60
           S  M  N  S  R  G  P  A  G  R  L  G  S  V  P  T  A  K  L  A         20
      AACGGCGACACCATCACCGGTCTCAACGCCATCATCAACGAGGCGTTCCTCGGCATTCCC            120
           N  G  D  T  I  T  G  L  N  A  I  I  N  E  A  F  L  G  I  P         40
      TTTGCCGAGCCGCCGGTGGGCAACCTCCGCTTCAAGGACCCTGTGCCGTACTCTGGCTCG            180
           F  A  E  P  P  V  G  N  L  R  F  K  D  P  V  P  Y  S  G  S         60
      CTCAACGGCCAGAAGTTCACTTCTTACGGCCCGTCTTGCATGCAGCAGAACCCCGAGGGC            240
           L  N  G  Q  K  F  T  S  Y  F  P  S  C  M  Q  Q  N  P  E  G         80
      ACGTTTGAAGAACCTTGGCAAGACGGCACTCGACTTGGTGATGCAGTCCAAGGTGTTC              300
           T  F  E  E  N  L  G  K  T  A  L  D  L  V  M  Q  S  K  V  F        100
      CAGGCGGTGCTTCCCCAGAGTGAGGACTGCCTCACCATCAACGTGGTGCGGCCGCCGGGC            360
           Q  A  V  L  P  Q  S  E  D  C  L  T  I  N  V  V  R  P  P  G        120
      ACCAAGGCGGGCGCCAACCTCCCGGTCATGCTCTGGATCTTTGGCGGTGGGTTTGAGATC            420
           T  K  A  G  A  N  L  P  V  M  L  W  I  F  G  G  G  F  E  I        140
      GGCAGCCCCACCATCTTCCCTCCCGCCCAGATGGTCACCAAGAGTGTGCTCATGGGCAAG            480
           G  S  P  T  I  F  P  P  A  Q  M  V  T  K  S  V  L  M  G  K        160
      CACATCATCCACGTGGCCGTCAACTACCGTGTTGCCTCGTGGGGGGTTCTTGGCTGGTGAT          540
           H  I  I  H  V  A  V  N  Y  R  V  A  S  W  G  F  L  A  G  D        180
      GACATCAAGGCCGAGGGCAGCGGGAACGCCGGCTTGAAGGACCAGCGTTTGGGCATGCAG            600
           D  I  K  A  E  G  S  G  N  A  G  L  K  D  Q  R  L  G  M  Q        200
      TGGGTGGCAGACAACATTGCCGGGTTCGGCGGCGACCCGAGCAAGGTGACTATCTTTGGC            660
           W  V  A  D  N  I  A  G  F  G  G  D  P  S  K  V  T  I  F  G        220
      GAGTCTGCGGGCAGCATGTCCGTGTTGTGCCACCTCATCTGGAACGACGGCGACAACACG            720
           E  S  A  G  S  M  S  V  L  C  H  L  I  W  N  D  G  D  N  T        240
      TACAAGGGCAAGCCGTTGTTCCGCGCGGGCATCATGCAGTCTGGAGCCATGGTGCCGTCT            780
           Y  K  G  K  P  L  F  R  A  G  I  M  Q  S  G  A  M  V  P  S        260
      GACCCGGTGGACGGCACGTACGGCAACGAGATCTACGACCTCTTTGTCTCGAGTGCTGGC            840
           D  P  V  D  G  T  Y  G  N  E  I  Y  D  L  F  V  S  S  A  G        280
      TGTGGCAGCGCCAGCGACAAGCTCGCGTGCTTGCGCAGTGCGTCTAGCGACACCTTGCTC            900
           C  G  S  A  S  D  K  L  A  C  L  R  S  A  S  S  D  T  L  L        300
      GATGCCACCAACAACACTCCTGGGTTCTTGGCGTACTCCTCGTTGCGGTTGTCTTATCTC            960
           D  A  T  N  N  T  P  G  F  L  A  Y  S  S  L  R  L  S  Y  L        320
      CCGCGGCCCGACGGCAAGAACATCACCGATGACATGTACAAGTTGGTGCGCGACGGCAAG           1020
           P  R  P  D  G  K  N  I  T  D  D  M  Y  K  L  V  R  D  G  K        340
      TATGCAAGCGTTCCCGTGATCATTGGCGACCAGAACGACGAGGGCACCATCTTTGGCTC            1080
           Y  A  S  V  P  V  I  I  G  D  Q  N  D  E  G  T  I  F  G  L        360
      TCTTCTTTGAACGTGACCACGAATGCTCAGGCCCGTGCTTACTTCAAGCAGTCTTTCATC           1140
           S  S  L  N  V  T  T  N  A  Q  A  R  A  Y  F  K  Q  S  F  I        380
      CACGCCAGCGACGCGGAGATCGACACCTTGATGGCGGCGTACCCCCAGGACATCACCCAG           1200
           H  A  S  D  A  E  I  D  T  L  M  A  A  Y  P  Q  D  I  T  Q        400
      GGTTCTCCGTTCGACACCGGCGTGTTCTCAACGCCCTCACCCCGCAGTTCAAGAGAATCTCT         1260
           G  S  P  F  D  T  G  V  L  N  A  L  T  P  Q  F  K  R  I  S        420
      GCGGTGCTTCGGCGACCTTGCATTCATCCACGCCCGCCGCTACTTCCTCAACCACTTCCAG         1320
           A  V  L  G  D  L  A  F  I  H  A  R  R  Y  F  L  N  H  F  Q        440
      GGCGGCACCAAGTACTCGTTCCTTCTAAGCAGCTCTGGGTTGCCAATCATGGGCACC             1380
           G  G  T  K  Y  S  F  L  S  K  Q  L  S  G  L  P  I  M  G  T        460
      TTCCATGCCAACGACATTGTGTGGCAGGACTACTTGTTGGGAAGCGGCAGCGTCATCTAC          1440
           F  H  A  N  D  I  V  W  Q  D  Y  L  L  G  S  G  S  V  I  Y        480
      AACAACGCGTTTATCGCGTTCGCCACCGACTTGGACCCCAACACCGCGGGGTTGTTGGTG          1500
           N  N  A  F  I  A  F  A  T  D  L  D  P  N  T  A  G  L  L  V        500
      AACTGGCCCAAGTACACCAGCAGCTCTCAGTCTGGCAACAACTTGATGATGATCAACGCC          1560
           N  W  P  K  Y  T  S  S  S  Q  S  G  N  N  L  M  M  I  N  A        520
      TTGGGCTTGTACACCGGCAAGGACAACTTCCGCACCGCTGGCTACGACGCGTTGATGACC          1620
           L  G  L  Y  T  G  K  D  N  F  R  T  A  G  Y  D  A  L  M  T        540
      AACCCGTCTTCTTTCTTTGTG                     (SEQ ID NO:3)                 1641
           N  P  S  S  F  F  V                  (SEQ ID NO:4)                 547
```

```
Mutant C. rugosa lipase 4
TCGATGAATTCACGTGGCCCAGCCGGCCGTCTCGGATCGGTACCCACTGCCACGCTCGCC    60
 S  M  N  S  R  G  P  A  G  R  L  G  S  V  P  T  A  T  L  A    20
AACGGCGACACCATCACCGGTCTCAACGCCATCATCAACGAGGCGTTCCTCGGTATTCCC   120
 N  G  D  T  I  T  G  L  N  A  I  I  N  E  A  F  L  G  I  P    40
TTTGCTCAGCCGCCGGTGGGCAACCTCCGCTTCAAGCCGCCTGTGCCGTACTCGGCGTCT   180
 F  A  Q  P  P  V  G  N  L  R  F  K  P  P  V  P  Y  S  A  S    60
CTCAATGGTCAGAAGTTTACTTCGTATGGCCCTTCGTGCATGCAGATGAACCCATTGGGC   240
 L  N  G  Q  K  F  T  S  Y  G  P  S  C  M  Q  M  N  P  L  G    80
AACTGGGACTCCTCGCTTCCCAAGGCTGGCATCAACTCCTTGATGCAGTCCAAGCTCTTC   300
 N  W  D  S  S  L  P  K  A  A  I  N  S  L  M  Q  S  K  L  F   100
CAGGCGGTGCTTCCTAACGGCGAGGACTGTCTCACCATCAACGTGGTGCGGCCGTCAGGC   360
 Q  A  V  L  P  N  G  E  D  C  L  T  I  N  V  V  R  P  S  G   120
ACCAAHCCHHHTHCCAACCTCCCCCGTGATGGTGTGGATTTTTGCGGCGGGTTTGAGGTT   420
 T  K  P  G  A  N  L  P  V  M  V  W  I  F  G  G  G  F  E  V   140
GGCGGCTCCAGTCTCTTCCCTCCCGCACAGATGATCACCGCCAGCGTGCTTATGGGCAAG   480
 G  G  S  S  L  F  P  P  A  Q  M  I  T  A  S  V  L  M  G  K   160
CCCATCATCCACGTGAGCATGAACTACCGCGTTGCTTCGTGGGGGTTCTTGGCTGGTCCA   540
 P  I  I  H  V  S  M  N  Y  R  V  A  S  W  G  F  L  A  G  P   180
GACATCAAGGCCGAGGGCAGCGGGAACGCCGGTTTGCACGACCAACGCTTGGGTTTGCAG   600
 D  I  K  A  E  G  S  G  N  A  G  L  H  D  Q  R  L  G  L  Q   200
TGGGTGGCGGACAACATTGCCGGGTTCGGCGCGACCCGTCCAAGGTGACCATCTTTGGT   660
 W  V  A  D  N  I  A  G  F  G  G  D  P  S  K  V  T  I  F  G   220
GAGTCGGCGGGCAGCATGTCGGTAATGTGTCAGCTCCTCTGGAACGACGGCGACAACACG   720
 E  S  A  G  S  M  S  V  M  C  Q  L  L  W  N  D  G  D  N  T   240
TACAACGCAAGCCGTTGTTCCGTGCCGCCATCATGCAGTTCTGGGGCCATGGTGCCGTCG   780
 Y  N  G  K  P  L  F  R  A  A  I  M  Q  S  G  A  M  V  P  S   260
GACCCGGTGGATGGGCCCTACGGCACGCAGATCTACGACCAGGTGGTTGCTTCAGCCGGC   840
 D  P  V  D  G  P  Y  G  T  Q  I  Y  D  Q  V  V  A  S  A  G   280
TGTGGCAGTGCCAGCGACAAGCTCGCGTGCTTGCGCAGCATCGAACGACAAACTCTTC    900
 C  G  S  A  S  D  K  L  A  C  L  R  S  I  S  N  D  K  L  F   300
CAGGCCACCAGCGACACTCCGGGGGCCTTGGCGTACCCCTCGTTGCGGTTGTCGTTTCTC   960
 Q  A  T  S  D  T  P  G  A  L  A  Y  P  S  L  R  L  S  F  L   320
CCGCGGCCCGACGGCACCTTCATCACCGATGACATGTTCAAGTTGGTGCGCGACGGCAAG  1020
 P  R  P  D  G  T  F  I  T  D  D  M  F  K  L  V  R  D  G  K   340
TGTGCCAACGTTCCGGTGATCATTGGCGACCAGAACGACGAGGGCACAGTGTTTGCGTTG  1080
 C  A  N  V  P  V  I  I  G  D  Q  N  D  E  G  T  V  F  A  L   360
TCCAGCTTGAACGTGACTACGGATGCTCAGGCACGCCAGTACTTCAAGGAAAGCTTCATC  1140
 S  S  L  N  V  T  T  D  A  Q  A  R  Q  Y  F  K  E  S  F  I   380
CACGCCAGCGACGCGGAGATCGACACCTTGATGGCGGCGTACCCCAGCGACATCACCCAG  1200
 H  A  S  D  A  E  I  D  T  L  M  A  A  Y  S  P  D  I  T  Q   400
GGTAGTCCGTTCGACACCGGCATCTTCAACGCCATCACCCCGCAGTTCAAACGGATTGCA  1260
 G  S  P  F  D  T  G  I  F  N  A  I  T  P  Q  F  K  R  I  A   420
GCGGTGCTTGGTGACCTTGCGTTCACTCTCCCCCGGCGCTACTTCCTCAACCACTTCCAG  1320
 A  V  L  G  D  L  A  F  T  L  P  R  R  Y  F  L  N  H  F  Q   440
GGCGGCACCAAGTACTCGTTCCTCTCGAAGCAGCTTAGTGGGTTGCCGGTGATTGGCACC  1380
 G  G  T  K  Y  S  F  L  S  K  Q  L  S  G  L  P  V  I  G  T   460
CACCACGCCAACGACATTGTGTGGCAGGACTTTTTGGTGAGCCACAGCAGCGCCGTGTAC  1440
 H  H  A  N  D  I  V  W  Q  D  F  L  V  S  H  S  S  A  V  Y   480
AACAACGCGTTTATTGCCTTTGCCAACGACCTCGACCCGAACAAGGCCGGTTTGCTTGTG  1500
 N  N  A  F  I  A  F  A  N  D  L  D  P  N  K  A  G  L  L  V   500
AACTGGCCCAAGTACACCAGCAGCTCTCAGTCAGGCAACAACTTGTTGCAGATCAACGCC  1560
 N  W  P  K  Y  T  S  S  S  Q  S  G  N  N  L  L  Q  I  N  A   520
TTGGGCTTGTACACCGGCAAGGACAACTTCCGCACCGCTGGCTACGACGCGTTGTTTACC  1620
 L  G  L  Y  T  G  K  D  N  F  R  T  A  G  Y  D  A  L  F  T   540
AACCCGTCTTCTTTCTTTGTRG  (SEQ ID NO:5)                         1641
 N  P  S  S  F  F  V  (SEQ ID NO:6)                            547
```

-continued

Mutant *C. rugosa* lipase 5

```
TCGATGAATTCACGTGGCCCAGCCGGCCGTCTCGGATCGGTACCCACTGCCACGCTCGCC      60
 S  M  N  S  R  G  P  A  G  R  L  G  S  V  P  T  A  T  L  A       20
AACGGCGACACCATCACCGGTCTCAACGCCATCATCAACGAGGCGTTCCTCGGCATTCCC     120
 N  G  D  T  I  T  G  L  N  A  I  I  N  E  A  F  L  G  I  P       40
TTTGCCGAGCCGCCGGTGGGCAACCTCCGCTTCAAGGACCCTGTGCCGTACCGTGGGTCT     180
 F  A  E  P  P  V  G  N  L  R  F  K  D  P  V  P  Y  R  G  S       60
CTCAACGGTCAATCCTTCACCGCGTACGGTCCGTCTTGCATGCAGCAGAACCCCGAGGGC     240
 L  N  G  Q  S  F  T  A  Y  G  P  S  C  M  Q  Q  N  P  E  G       80
ACCTACGAGGAGAACCTCCCCAAGGTGGCGCTTGACTTGGTGATGCAGTCCAAGGTGTTC     300
 T  Y  E  E  N  L  P  K  V  A  L  D  L  V  M  Q  S  K  V  F      100
CAGGCTGTTCTCCCCAACAGCGAGGACTGCCTCACCATCAACGTGGTGCGGCCGCCGGGC     360
 Q  A  V  L  P  N  S  E  D  C  L  T  I  N  V  V  R  P  P  G      120
ACCAAGGCGGGCGCCAACCTCCCGGTCATGCTCTGGATCTTTGGCGGTGGGTTTGAGATC     420
 T  K  A  G  A  N  L  P  V  M  L  W  I  F  G  G  G  F  E  I      140
GGCAGCCCCACCATCTTCCCTCCCGCTCAGATGGTCTCCAAGAGTGTGCTCATGGGCGAG     480
 G  S  P  T  I  F  P  P  A  Q  M  V  S  K  S  V  L  M  G  E      160
CCCATCATCCACGTGGCCGTCAACTACCGCTTGGCGTCCTTTGGTTTCTTGGCCGGTCCG     540
 P  I  I  H  V  A  V  N  Y  R  L  A  S  F  G  F  L  A  G  P      180
GACATCAAGGCCGAGGGCAGCTCCAATGCCGGCCTCAAGGACCAGCGCTTGGGCATGCAG     600
 D  I  K  A  E  G  S  S  N  A  G  L  K  D  Q  R  L  G  M  Q      200
TGGGTGGCGGACAACATTGCCGGGTTCGGCGGCGACCCGTCCAAGGTGACCATCTTTGGC     660
 W  V  A  D  N  I  A  G  F  G  G  D  P  S  K  V  T  I  F  G      220
GAGTCTGCGGGCAGCATGTCCGTGTTGTGCCACCTTCTCTGGAATGGCGGCGACAACACG     720
 E  S  A  G  S  M  S  V  L  C  H  L  L  W  N  G  G  D  N  T      240
TACAAGGGCAAGCCGTTGTTCCGCGCGGGCATCATGCAGTCTGGAGCCATGGTGCCGTCT     780
 Y  K  G  K  P  L  F  R  A  G  I  M  Q  S  G  A  M  V  P  S      260
GACCCGGTGGACGGCACCTATGGAGCCCAAATCTATGACACGTTGGTGGCTTCTACGGGT     840
 D  P  V  D  G  T  Y  G  A  Q  I  Y  D  T  L  V  A  S  T  G      280
TGCAGCAGTGCCAGCAACAAGCTTGCGTGCTTGCGTGGTCTTTCTACTCAGGCATTGCTC     900
 C  S  S  A  S  N  K  L  A  C  L  R  G  L  S  T  Q  A  L  L      300
GATGCCACCAACGACACCCCTGGGTTCTTGTCGTACACCTCGTTGCGGTTGTCTTATCTC     960
 D  A  T  N  D  T  P  G  F  L  S  Y  T  S  L  R  L  S  Y  L      320
CCGCGGCCCGACGGCGCCAACATCACCGATGACATGTACAAGTTGGTACGCGACGGCAAG    1020
 P  R  P  D  G  A  N  I  T  D  D  M  Y  K  L  V  R  D  G  K      340
TATGCAAGCGTTCCCGTGATCATTGGCGACCAGAACGACGAGGGCTTCTTGTTTGATCTC    1080
 Y  A  S  V  P  V  I  I  G  D  Q  N  D  E  G  F  L  F  D  L      360
TCTTCTTTGAACACCACCACCGAGGCCGACGCCGAGGCATACCTCAGAAAGTCTTTCATC    1140
 S  S  L  N  T  T  T  E  A  D  A  E  A  Y  L  R  K  S  F  I      380
CACGCCACCGACGCCGATATCACCGCATTGAAGGCGGCGTACCCCAGCGATGTCACCCAG    1200
 H  A  T  D  A  D  I  T  A  L  K  A  A  Y  P  S  D  V  T  Q      400
GGTTCTCCGTTCGACACGGGCATTCTCAACGCCCTTACACCCCAGCTCAAGCGGATCAAT    1260
 G  S  P  F  D  T  G  I  L  N  A  L  T  P  Q  L  K  R  I  N      420
GCTGTGCTTGGCGACCTCACCTTTACCCTCTCGCGCCGCTACTTCCTCAACCACTACACC    1320
 A  V  L  G  D  L  T  F  T  L  S  R  R  Y  F  L  N  H  Y  T      440
GGTGGTCCCAAGTACTCGTTCCTCTCTAAGCAGCTTTCTGGGTTGCCCATTCTCGGTACG    1380
 G  G  P  K  Y  S  F  L  S  K  Q  L  S  G  L  P  I  L  G  T      460
TTCCACGCGAACGACATTGTGTGGCAGCACTTTTTGTTGGGCAGCGGCAGCGTCATCTAC    1440
 F  H  A  N  D  I  V  W  Q  H  F  L  L  G  S  G  S  V  I  Y      480
AACAACGCGTTCATCGCGTTTGCCACCGACTTGGACCCCAACACCGCGGGCTTGTCTGTG    1500
 N  N  A  F  I  A  F  A  T  D  L  D  P  N  T  A  G  L  S  V      500
CAGTGGCCCAAGTACACCAGCAGCTCTCAGGCGGGGGACAACTTGATGCAGATCAGTGCC    1560
 Q  W  P  K  Y  T  S  S  S  Q  A  G  D  N  L  M  Q  I  S  A      520
TTGGGCTTGTACACCGGCAAGGACAACTTCCGCACCGCCGGCTACAACGCTTTGTTTGCC    1620
 L  G  L  Y  T  G  K  S  N  F  R  T  A  G  Y  N  A  L  F  A      540
GACCCGTCTCACTTTTTCGTG (SEQ ID NO:7)                              1641
 D  P  S  H  F  F  V   (SEQ ID NO:8)                              547
```

Muatant *C. rugosa* lipase 8

```
TCGATGAATTCACGTGGCCCAGCCGGCCGTCTCGGATCGGTACCCACTGCCACGCTCGCC      60
 S  M  N  S  R  G  P  A  G  R  L  G  S  V  P  T  A  T  L  A       20
AACGGCGACACCATCACCGGTCTCAACGCCATCATCAACGAGGCGTTCCTCGGCATTCCC     120
 N  G  D  T  I  T  G  L  N  A  I  I  N  E  A  F  L  G  I  P       40
TTTGCCCAGCCGCCGGTGGGCAACCTCCGCTTCAAGGACCCCGTGCCGTACTCCGGCTCG     180
 F  A  E  P  P  V  G  N  L  R  F  K  D  P  V  P  Y  S  G  S       60
CTCGATGGCCAGAAGTTCACTTCTTACGGCCCGTCTTGCATGCAGCAGAACCCCGAGGGC     240
 L  D  G  Q  K  F  T  S  Y  G  P  S  C  M  Q  Q  N  P  E  G       80
ACCTACGAGGAGAACCTCCCCAAGGCAGCGCTCGACTTGGTCATGCAGTCCAAGGTGTTT     300
 T  Y  E  E  N  L  P  K  A  A  L  D  L  V  M  Q  S  K  V  F      100
GAGGCGGTGTCTCCGTCTAGCGAGGACTGTCTCACCATCAACGTGGTGCGGCCGCCGGGC     360
 E  A  V  S  P  S  S  E  D  C  L  T  I  N  V  V  R  P  P  G      120
ACCAAGGCGGGTGCCAACCTCCCGGTGATGCTCTGGATCTTTGGCGGCGGGTTTGAGGTG     420
 T  K  A  G  A  N  L  P  V  M  L  W  I  F  G  G  G  F  E  V      140
GGTGGCACCAGCACCTTCCCTCCCGCCCAGATGATCACCAAGAGCATTGCCATGGGCAAG     480
 G  G  T  S  F  P  P  A  Q  M  I  T  K  S  I  A  M  G  K      160
CCCATCATCCACGTGAGCGTCAACTACCGCGTGTCGTCGTGGGGGTTCTTGGCTGGCGAC     540
 P  I  I  H  V  S  V  N  Y  R  V  S  S  W  G  F  L  A  G  D      180
GAGATCAAGGCCGAGGGCAGTGCCAACGCCGGTTTGAAGGACCAGCGCATGGGCTGCAG     600
 E  I  K  A  E  G  S  A  N  A  G  L  K  D  Q  R  M  G  M  Q      200
TGGGTGGCGGACAACATTGCGGCGTTTGGCGGCGACCCGACCAAGGTGACCATCTTTGGC     660
 W  V  A  D  N  I  A  A  F  G  G  D  P  T  K  V  T  I  F  G      220
GAGTCTGCGGGCAGCATGTCGGTCATGTGCCACATTCTCTGGAACGACGGCGACAACACG     720
 E  S  A  G  S  M  S  V  M  C  H  I  L  W  N  D  G  D  N  T      240
TACAAGGGCAAGCCGCTCTTCCGCGCGGGCATCATGCAGTCTGGGGCCATGGTACCGTCG     780
 Y  K  G  K  P  L  F  R  A  G  I  M  Q  S  G  A  M  V  P  S      260
GACGCGGTGGACGGCGTCTACGGCAACGAGATCTTTGACCTCTTGGGGTCGACGCGGGC     840
 D  A  V  D  G  V  Y  G  N  E  I  F  D  L  L  A  S  D  A  G      280
```

-continued

```
TGCGGCAGCGCCAGCGACAAGCTTGCGTGCTTGCGCGGTGTGTCTAGCGACACGTTGGAG    900
 C   G   S   A   S   D   K   L   A   C   L   R   G   V   S   S   D   T   L   E      300
GACGCCACCAACAACACCCCTGGGTTCTTGGCGTACTCCTGGTTGCGGTTGTCTTATCTC    960
 D   A   T   N   N   T   P   G   F   L   A   Y   S   S   L   R   L   S   Y   L      320
CCGCGGCCCGACGGCGTGAACATCACCGACGACATGTTTGCCTTGGTCCGCGAGGGCAAG   1020
 P   R   P   D   G   V   N   I   T   D   D   M   F   A   L   V   R   E   G   K      340
TATGCAAGCGTTCCTGTGATCATCGGCGACCAGAACGACGAGGGCACCTTCTTTGGCACC   1080
 Y   A   S   V   P   V   I   I   G   D   O   N   D   E   G   T   F   F   G   T      360
TCTTCTTTGAACGTGACCACGGATGCCGAGGCCCGCCAGTACTTCAGGCAGTCTTTTGTC   1140
 S   S   L   N   V   T   T   D   A   E   A   R   Q   Y   F   T   Q   S   F   V      380
CACGCCAGCGACGCGGAGCTCGACACGTTGATGACGGCGTACCCCCAGGACATCACCCAG   1200
 H   A   S   D   A   W   L   D   T   L   M   T   A   Y   P   Q   D   I   T   Q      400
GGTTCTCCGTTCGACACGGGTGTTCTCAACGCCCTCACCCCGCAGTTCAAGAGAATCTCT   1260
 G   S   P   F   D   T   G   V   L   N   A   L   T   P   Q   R   K   R   I   S      420
GCGGTGCTCGGCGACCTTGCCTTCATCCACGCCCGTCGCTACTTCCTCAACCACTACACC   1320
 A   V   L   G   D   L   A   F   I   H   A   R   R   Y   F   L   N   H   Y   T      440
GGCGGCACCAAGTACTCATTCCTCTCTAAGCAGCTCTCTGGCTTGCCGGTGCTCGGAACG   1380
 G   G   T   K   Y   S   F   L   S   K   Q   L   S   G   L   P   V   L   G   D      460
TTCCACTCCAACGACATTGTCTTCCAGGACTACTTGTTGGGCAGCGGCTCGCTCATCTAC   1440
 F   H   S   N   D   I   B   F   Q   D   Y   L   L   G   S   G   S   L   I   Y      480
AACAACGCGTTCATTGCGTTTGCCACGGACTTGGACCCCAACACCGCGGGGTTGTTGGTG   1500
 N   N   A   F   I   A   F   A   T   D   L   D   P   N   T   A   G   L   L   V      500
AAGTGGCCCGAGTACACCAGCAGCTCTCAGTCTGGCAACAACTTGATGATGATCAACGCC   1560
 K   W   P   E   Y   T   S   S   S   Q   S   G   N   N   L   M   M   I   N   A      520
TTGGGCTTGTACACCGGCAAGGACAACTCCCGCACCGCCGGCTACGACGCGTTGTTCTCC   1620
 L   G   L   Y   T   G   K   D   N   S   R   T   A   G   Y   D   A   L   F   S      540
AACCCGCCGTCTTTCTTTGTG   (SEQ ID NO:9)                             1641
 N   P   P   S   F   F   V   (SEQ ID NO:10)                       547
```

The differences between each mutant DNA and its corresponding wild-type DNA are due to replacement of the CTG codons with the universal serine codons, and in addition, can be due to degeneracy of genetic codons, which results in a DNA variant encoding, based on universal codons, a wild type C. rugosa lipase or a functionally equivalent amino acid sequence thereof. An isolated nucleic acid containing such a mutant DNA can be used to clone and express the C. rugosa lipase in a common host cell. A DNA variant can possess the codons preferred by a particular prokaryotic or eukaryotic host. The codons may be selected to increase the rate at which expression of a polypeptide occurs in the prokaryotic or eukaryotic host in accordance with the frequency with which the codons are utilized by the host. The mutant DNA can further include such variations as nucleotide substitutions, deletions, inversions, or insertions on the wild-type DNA. The variations can modify the cloning, processing, and expression of the C. rugosa lipase.

The just-described mutant DNA can be prepared based on site-directed mutagenesis, introducing very specific nucleotide substitutions (i.e., mutations) at defined locations in a nucleic acid sequence. See, for example, Zoller and Smith (1983) *Meth. Enzymol.* 100: 468; and *Molecular Cloning, A Laboratory Manual* (1989) Sambrook, Fritsch and Maniatis, Cold Spring Harbor, N.Y., chapter 15. Alternatively, the mutant DNA may be synthesized, in whole or in part, using chemical methods well known in the art. See Caruthers et al. (1980) *Nucl. Acids Res. Symp. Ser.* 215-223, and Horn et al. (1980) *Nucl. Acids Res. Symp. Ser.* 225-232. In particular, introducing multiple mutations can be accomplished through various methods based on, e.g., polymerase chain reaction (PCR), ligase chain reaction (LCR), or overlap extension polymerase chain reaction. See Ge and Rudolph (1997) *BioTechniques* 22: 28-30.

The mutant DNA can encode a polypeptide of SEQ ID NO:2, 4, 6, 8, or 10. Alternatively, it can encode a polypeptide variant having an amino acid sequence that is 90% identical to, or differs by 1, 5, 10, 50, or more amino acid residues from, SEQ ID NO:2, 4, 6, 8, or 10. If alignment is needed for this comparison, the sequences should be aligned for maximum homology. The polypeptide variant is correlated with at least one catalytic activity of a polypeptide encoded by SEQ ID NO:2, 4, 6, 8, or 10, e.g., ester bond hydrolysis or esterification. A polypeptide variant may have "conservative" changes, wherein a substituted amino acid has similar structural or chemical properties. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). In some embodiments, a polypeptide variant may have "nonconservative" changes, e.g., replacement of a leucine with a methionine. Further, a polypeptide variant may also include amino acid deletions or insertions, or both. Guidance in determining which amino acid residues may be substituted, inserted, or deleted without abolishing the catalytic activity may be found using computer programs well known in the art, for example, DNASTAR software.

It is well known that cutinase is the smallest lipolytic enzyme with determined three-dimensional structure, and may be considered an esterase with a broader activity that also includes lipids. Based on the alignment of secondary structure (e.g., α-helix or β-strand), topology of the C. rugosa lipase polypeptide chain is similar to that of cutinase (the three dimensional structures of LIP1 and LIP3 have been determined. See, for example, Grochulski et al. (1993) *J. Biol. Chem.* 268: 12843-12847; and Ghosh et al. (1995) *Structure* 3: 279-288). Therefore, according to the common folding pattern of lipase (Cygler et al. (1997) *Methods in Enzymol* 284: 3-37), the minimal functional fragment of C. rugosa lipase within the range of residues 100-456 can be determined (e.g., the β2 strand to α8,9 helix, totally about 350 amino acids and 1070 nucleotides).

The polypeptide having the amino acid sequence of SEQ ID NO:2 differs from the wild-type C. rugosa lipase 2 a N-terminal peptide (i.e., SMNSRGPAGRLGS; SEQ ID NO:11), and 4 amino acids (i.e., A1V; T35S; R78L; H79D). The polypeptide having the amino acid sequence of SEQ ID NO:4 differs form the wild-type C. rugosa lipase 3 by the N-terminal peptide and 5 amino acids (i.e., A1V; P148H; I395V; F396L; I399L). The polypeptide having the amino acid sequence of SEQ ID NO:6 differs form the wild-type *C. rugosa* lipase 4 by the N-terminal peptide and 1 amino acid (i.e., A1V). The polypeptide having the amino acid sequence of SEQ ID NO:8 differs from the wild-type *C. rugosa* lipase 5 by the N-terminal peptide and 5 amino acids (i.e., A1V; K147E; T256A; G346D; S492Y). The polypeptide having the amino acid sequence of SEQ ID NO:10 differs from the wild-type *C. rugosa* lipase 1 by the N-terminal peptide and 17 amino acids (i.e., A1V; L184M; I253V; N265D; Y320F; N330S; I331V; Q357E; E360Q; K363T; I374L; G383Q; I395V; G414A; T416I; L417H; F517S).

The just-described polypeptide can be produced by using an expression vector that contains an isolated nucleic acid of this invention. As used herein, the term "vector" refers to a nucleic acid molecule capable of transporting another nucleic acid to which it has been linked and can include a plasmid, cosmid, or viral vector. A vector is capable of autonomous replication, and contains the nucleic acid of this invention in a form suitable for expression of the nucleic acid in a host cell. It includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory or inducible sequences. A vector can be designed for expression of a *C. rugosa* lipase in prokaryotic or eukaryotic cells, e.g., bacterial cells (e.g., *E. coli*), insect cells (e.g., using baculovirus expression vectors), yeast cells (e.g., *P. pastoris*), or mammalian cells. Suitable host cells are discussed further in Goeddel, (1990) *Gene Expression Technology: Methods in Enzymology* 185, Academic Press, San Diego, Calif. Expression of a *C. rugosa* lipase can be carried out with vectors containing constitutive or inducible promoters directing the expression of either fusion or non-fusion lipases. The fusion lipase may facilitate purification of soluble polypeptides. Fusion vectors add a number of amino acids to a polypeptide encoded therein, usually to the amino terminus of the polypeptide. Typical fusion expression vectors include pGEX (Pharmacia Biotech Inc; Smith and Johnson (1988) *Gene* 67:31-40), pMAL (New England Biolabs, Beverly, Mass.), and pRIT5 (Pharmacia, Piscataway, N.J.) which fuse glutathione S-transferase (GST), maltose E binding protein, or protein A, respectively, to the target polypeptide.

A vector can be introduced into host cells via conventional transformation or transfection techniques. As used herein, the terms "transformation" and "transfection" refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporataon. A host cell of the invention can be used to express a *C. rugosa* lipase. The expressed *C. rugosa* lipase can be isolated from the host cell or a culture medium.

The present invention also provides a chimeric *C. rugosa* lipase that contains a substrate interacting domain of an isozyme and a non-substrate interacting domain of another isozyme. The "substrate interacting domain" refers to a fragment that is characterized by an approximated 32 amino acid sequence (e.g., amino acids of 63-94 of SEQ ID NO:8), and participates in substrate interactions. The "non-substrate interacting domains" include at least one catalytic domain, such as a carboxylesterase domain. The substrate interacting domain can be a part of the substrate binding region, which is generally dispersed along the full length amino acid sequence, and forms a tunnel to interact with, e.g., fatty acyl chain. See Cygler et al. (1999) *Biochim. Biophys. Acta* 1441: 205-214.

The carboxylesterase domain can catalyze hydrolysis of carboxylic esters, and include a catalytic triad: a serine, a glutamate (or aspartate), and a histidine. The sequence around the active site serine is well conserved and can be used as a signature pattern. See, e.g., Krejci et al. (1991) *Proc. Natl. Acad. Sci. USA* 88: 6647-6651(1991), or Cygler et al. (1993) *Protein Sci.* 2: 366-382. The chimeric polypeptide of this invention can be prepared by a domain shuffling method. For example, the method includes exchanging the SphI (184)-BstXI (304) restriction DNA fragments to obtain a recombinant nucleic acid encoding a mature chimeric *C. rugosa* lipase. The mature lipase contains a substrate interacting domain of an isozyme and non-substrate interacting sequences of another isozyme (e.g., LIP4). The recombinant nucleic acid is then ligated into a vector, e.g., pET-23a(+) *E. Coli*. T7 expression vector (Novagen) between Nde I and EcoRI sites.

Each of the just-described domains has at least 70% (e.g., 80%, 90%, 95%, or 100%) homology with its corresponding wild-type sequence, as long as its intended function in the chimeric polypeptide is retained. The chimeric polypeptide can be produced as a fusion chimeric polypeptide, e.g., a thioredoxin fused to the N-terminal of a chimeric polypeptide.

The specific example below is to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Expression of *C. rugosa* Lipase 2 (LIP2)

Materials and Methods

Strains and plasmids Plasmid-containing transformants were mainly grown in Luria-Bertani (LB) broth supplemented with ampicillin (100 μg/mL). The *P. pastoris* expression vector pGAPZαC (Invitrogen, Carlsbad, Calif.) was manipulated in *E. coli* strain TOP 10' grown in low salt Luria-Bertani (LB) broth (1% tryptone, 0.5% yeast extract, and 0.5% NaCl, pH 7.5) supplemented with zeocin (25 μg/mL). *P. pastoris* X-33 (wild type) was used for the expression of LIP2, and its transformants were cultured with YPD (0.1% yeast extract, 0.2% peptone, and 0.2% dextrose; pH 7.2) containing 100 μg/mL zeocin at 26° C.

Construction of expression vector. LIP2 has been sequenced previously (EMBL Databank accession number X64704). A PCR product containing the entire LIP2 coding region with a Kpn I restriction site at the 5' end and Not I site at the 3' end was prepared and cloned into the Kpn I-Not I sites of the *P. pastoris* expression vector pGAPZαC to generate pGAPZα-LIP2.

Transformation of plasmid DNAs into *P. pastoris*. Plasmid DNA (10 μg) harboring the engineered lipase gene was digested with EcoRV in a total volume of 20 μL for 2 h. Linearized plasmid was transformed into *P. pastoris* by the electroporation method. High voltage pulses (1.5 kV) were delivered to 100 μL samples in 0.2 cm electrode gap cuvettes (Bio-Rad Laboratories) by using a GENE PULSER apparatus with the Pulse Controller (Bio-Rad Laboratories). Individual colonies of transformants were pitched and patched on tributyrin-emulsion YPD plates. The lipase-secreting transformants were identified by the clear zone on the opaque tributyrin emulsion. *P. pastoris* transformed with pGAPZαC was used as a negative control.

Purification of recombinant LIP2. The culture medium from *P. pastoris* was concentrated by ultrafiltration on a 30,000 molecular weight cut-off membrane. These samples were then applied onto a HIPREP 61/10 Octyl FF column (Pharmacia Biotech). The column was washed with 5 column volumes of TE buffer plus 1 mM CHAPS and then 4 mM CHAPS. Bound proteins were then eluted with 5 column volumes of TE buffer containing 30 mM CHAPS. The eluted materials were dialyzed against TE buffer.

The eluted proteins were then applied to a HIPREP 16/10 Q XL column (Pharmacia Biotech) equilibrated with TE buffer and the proteins were eluted using a linear gradient of 0 to 300 mM $(NH_4)_2SO_4$ over 5 column volumes. Protein concentrations in the fractions were measured with the Bio-Rad assay kit and esterase activity was determined using p-nitrophenyl butyrate as a substrate. Purified proteins were stored in a storage buffer (60 mM KCl, 10 mM Tris-HCl, 1.25 mM EDTA, 1% Triton X-100, and 17% glycerol, pH 7.5) at -20° C.

Enzyme characterization. The molecular masses of the purified recombinant LIP2 and a commercial lipase (Lipase Type VII, Sigma) were determined by SDS-PAGE analysis. To analyze the thermal stability of lipase, samples were incubated at various temperatures from 37 to 100° C. for 10 minutes, and the residual activities were determined by spectrophotometric method (Redondo et al. (1995) *Biochim. Biophys. Acta* 1243 :15-24), using p-nitrophenyl caprylate as a substrate at 37° C. The optimal reaction temperature for lipase was investigated at different temperatures from 10 to 60° C., and the activity was measured by spectrophotometric method using p-nitrophenyl butyrate as a substrate at pH 7.0. The optimal reaction pH for lipase was investigated at different pH from 3.0 to 9.0, and the activity was measured by spectrophotometric method using p-nitrophenyl butyrate as a substrate at 37° C.

The lipase activities were measured by titrimetry using triglycerides with various chain-length fatty acids as substrates. See Wang et al. (1988) *Biotechnol. Bioeng.* 31: 628-633. The release of free fatty acid was continuously monitored by titration with 1 mM NaOH on the pH-Stat. The esterase activity at 37° C. was determined spectrophotometrically using p-nitrophenyl esters as substrates. One unit of activity was defined as the smallest amount of enzyme able to release 1 μmol of p-nitrophenol per minute.

Results

Construction of Expression Plasmids and Overexpression of Recombinant LIP2 All 17 CTG codons of LIP2 gene were replaced with universal Ser codons (TCT) by simultaneous multiple site-directed mutagenesis. See Ge and Rudolph (1997) *BioTechniques.* 22: 28-30. The plasmid harboring the engineered LIP2 was transformed into *P. pastoris* by electroporation. The transformant cells were grown in 500-mL flasks containing 200 mL YPD medium for three days. The constitutive strong promoter of glyceraldehydes 3-phosphate dehydrogenase (GAP) allows the high level expression of LIP2. The majority of expressed LIP2 was secreted into the culture medium and the estimated amount of LIP2 was 2.3 mg/L. The transformants are highly stable and the produced LIP2 would be greatly increased in high cell density fermentation. See Cereghino and Cregg (2000) *FEMS Microbiol. Rev.* 24: 45-66.

Biochemical characterization of recombinant LIP2 The optimal pH of LIP2 was 7 and the enzyme showed 90% of activity at pH 6. In contrast, the optimal pHs of LIP4 and a commercial *C. rugosa* lipase (CRL) were pH 7-8 and 8, respectively. LIP2 showed much higher specific activity than LIP4 and CRL with p-nitrophenyl butyrate at all pH tested, especially at pH 6. The ratio of specific activity of LIP2, LIP4 and CRL was 100:4:3 at pH 6, whereas it was 100:80:25 at pH 8. Therefore, the LIP2 is especially useful at slightly acidic to neutral pH for industrial applications.

Further, the optimal temperatures for LIP2, LIP4 and CRL were 40-50, 40 and 37° C., respectively. The LIP2 showed broad optimum temperature range 30-50° C. and much higher specific activity than LIP4 and CRL at all temperature tested (10-60° C.). Unexpectedly, LIP2 showed quite high activity at low temperature, e.g., the specific activity at 10° C. was 1000 U/mg, which was 50% of that at optimum temperature. This suggested that the enzyme could be applied to the synthesis of labile compounds and low boiling point compounds at low temperature.

The enzyme activities after heating at various temperatures for 10 min were also compared. The LIP2 was more stable than either LIP4 or CRL at 50-70° C. After 10 min heating at 70° C., the residual activities for LIP2, LIP4 and CRL were 80%, 50% and 35%, respectively.

For the hydrolysis of p-nitrophenyl esters of various chain-length fatty acids (Table 1), LIP2, LIP4 and CRL showed different preference to ester substrates. The best substrates for LIP2, LIP4 and CRL were p-nitrophenyl palmitate, p-nitrophenyl palmitate and p-nitrophenyl caprylate, respectively. Both LIP2 and LIP4 showed much higher activity toward medium to long chain fatty acid esters ($C_{12}$-$C_{18}$), but LIP2 had 2-3 times higher activity than LIP4. For most the p-nitrophenyl esters including p-nitrophenyl butyrate, -caprylate, -caprate, -laurate, -myristate, -palmitate and -stearate, the specific activities were in the order: LIP2>LIP4>CRL.

Hydrolysis activities of triglycerides One important industrial application of lipases is the hydrolysis of fat and vegetable oils, which occur naturally as triglycerides, to produce fatty acids. See, e.g., Shaw et al. (1990) *Biotechnol. Bioeng.* 35: 132-137. Table 2 showed LIP2, LIP4 and CRL had different preference to triglyceride substrates. The best triglyceride substrates for LIP2, LIP4 and CRL were tributyrin, tricaprylin and tricaprylin, respectively.

For tributyrin, trilaurin, tripalmitin, tristearin and triolein, the specific activity of hydrolysis was in the following order: LIP2>LIP4>CRL. For triacetin and tricaproin, the order was LIP2>CRL>LIP4. For tricaprylin, the order was: LIP4>CRL>LIP2. For tricaprin and trimyristin, the order was: CRL>LIP2>LIP4. Therefore, different LIP isoforms should be used for different industrial applications in triglyceride hydrolysis.

Cholesterol esterase activity As shown in Table 3, LIP2 showed much higher specific activity of cholesterol esterase than LIP4 and CRL among three cholesteryl esters tested. Among various cholesteryl esters, cholesteryl laurate was the best substrate hydrolyzed by LIP2. Therefore, the LIP2 can be used as a useful cholesterol esterase for the applications in clinical chemistry, biochemistry and food analysis. Since about 70-80% of serum cholesterol is esterified with various chain-length and saturated fatty acids (Röschlau et al. (1974) 12: 403-407), therefore LIP2, which has cholesterol esterase activity, can be used for coupling with cholesterol oxidase and peroxidase to determine the serum cholesterol enzymatically. The high specific activity of LIP2 toward the various cholesteryl esters allows very efficient and accurate determination of the cholesterol esters in serum and food.

Synthesis of esters Lipase can efficiently catalyze the synthesis of various esters for industrial applications such as fruit-flavored products (e.g. beverages, candies, jellies, and jams), baked goods, wines, dairy products (e.g. cultured butter, sour cream, yogurt, and cheese), emulsifiers, lubricants and cosmetics. See, for example, Kim et al. (1998) *J. Am. Oil Chem. Soc.* 75: 1109-1113; Shaw and Lo (1994) *J. Am. Oil Chem. Soc.* 71: 715-719; or Shaw et al. (1991) *Enzyme Microb. Technol.* 13: 544-546. Table 4 showed that LIP2 was much better than either LIP4 or CRL in the synthesis of hexadecyl of octadecyl myristate, suggesting it favored long-chain alcohols in the esterification of myristic acid with equimolar mixtures of different alcohols. In contrast, CRL was the best for the synthesis of hexyl-, octyl- and dodecyl-myristate, suggesting it favored medium to short chain alcohols for myristic ester synthesis.

Table 5 showed that LIP2 had much higher activity for the synthesis of propyl butyrate than either LIP4 or CRL, suggesting it favored short chain acids in the esterification of n-propanol with equimolar mixtures of different chain length fatty acids. In contrast, LIP4 was the best for the synthesis of propyl dodecanoate, hexadecanoate and octadecanoate, suggesting it favored medium to long chain fatty acids for propyl ester synthesis.

TABLE 1

Hydrolysis of p-nitrophenyl (p-NP) esters of various chain-length fatty acids.

|  | LIP2 | LIP4 | CRL |
|---|---|---|---|
|  | (U/mg$^a$) | | |
| p-NP acteate (C2) | 11 ± 1 (0.4)$^b$ | 10 ± 1 (0.7) | 16 ± 2 (3.1) |
| p-NP butyrate (C4) | 1986 ± 30 (72) | 899 ± 20 (63) | 359 ± 42 (72) |
| p-NP caproate (C6) | 108 ± 15 (4) | 151 ± 13 (11) | 72 ± 5 (14) |
| p-NP caprylate (C8) | 978 ± 126 (35) | 504 ± 24 (35) | 498 ± 67 (100) |
| p-NP caprate (C10) | 1453 ± 210 (53) | 1295 ± 179 (91) | 395 ± 19 (79) |
| p-NP laurate (C12) | 2567 ± 277 (93) | 867 ± 41 (61) | 269 ± 44 (54) |
| p-NP myristate (C14) | 2567 ± 277 (93) | 1140 ± 41 (80) | 372 ± 5 (75) |
| p-NP palmitate (C16) | 2766 ± 4 (100) | 1429 ± 127 (100) | 317 ± 5 (64) |
| p-NP stearate (C18) | 1580 ± 21 (57) | 580 ± 21 (41) | 67 ± 1 (13) |

$^a$The unit (U) definition: One unit of activity is the amount of enzyme necessary to hydrolyze 1.0 micromole of p-nitrophenyl ester per min at 37° C. and pH 7.0.
$^b$The parentheses represent the ratio of the activity of each substrate to the highest one for the same enzyme.

TABLE 2

Hydrolysis of triglyceride of various chain-length fatty acids.

|  | LIP2 | LIP4 | CRL |
|---|---|---|---|
|  | (U/mg$^a$) | | |
| Triacetin (C2) | 39 ± 1 (2)$^b$ | 10 ± 1 (0) | 11 ± 1 (0) |
| Tribytyrin (C4) | 2540 ± 60 (100) | 1138 ± 10 (28) | 1029 ± 64 (33) |
| Tricaproin (C6) | 599 ± 37 (24) | 167 ± 7 (4) | 358 ± 14 (11) |
| Tricaprylin (C8) | 1239 ± 31 (49) | 4082 ± 298 (100) | 3118 ± 190 (100) |
| Tricaprin (C10) | 1399 ± 176 (55) | 628 ± 11 (15) | 2160 ± 75 (69) |
| Trilaurin (C12) | 1743 ± 110 (69) | 389 ± 4 (10) | 1502 ± 8 (48) |
| Trimyristin (C14) | 504 ± 33 (20) | 375 ± 33 (9) | 915 ± 26 (29) |
| Tripalmitin (C16) | 54 ± 6 (2) | 151 ± 10 (4) | 137 ± 12 (4) |
| Tristearin (C18) | 422 ± 9 (17) | 348 ± 38 (9) | 39 ± 2 (1) |
| Triolein (C18:1) | 513 ± 4 (20) | 352 ± 5 (9) | 303 ± 24 (10) |

$^a$The unit (U) definition: One unit of activity is the amount of enzyme necessary to hydrolyze 1.0 micromole of ester bond per min at 37° C. and pH 7.0.
$^b$The parentheses represent the ratio of the activity of each substrate to the highest one for the same enzyme.

TABLE 3

Hydrolysis of cholesterol esters of various chain-length fatty acids.

|  | LIP2 | LIP4 | CRL |
|---|---|---|---|
|  | ($10^{-2}$ U/mg$^a$) | | |
| Cholesteryl n-butyrate (C4) | 127.1 ± 1.4 (32)$^b$ | 24.7 ± 1.3 (25) | 7.3 ± 0.1 (53) |
| Cholesteryl laurate (C12) | 402.0 ± 35.5 (100) | 98.2 ± 3.2 (100) | 13.8 ± 0.5 (100) |
| Cholesteryl stearate (C18) | 127.1 ± 1.4 (32) | 45.0 ± 1.8 (46) | 6.5 ± 0.7 (47) |

$^a$The unit (U) definition: One unit of activity is the amount of enzyme necessary to hydrolyze 1.0 micromole of cholesteryl ester per min at 37° C. and pH 7.0.
$^b$The parentheses represent the ratio of the activity of each substrate to the highest one for the same enzyme.

TABLE 4

Esterification of myristic acid with various chain-length alcohols.

|  | LIP2 | LIP4 | CRL |
|---|---|---|---|
|  | ($10^3$ μmol/h/mg)$^a$ | | |
| n-hexyl myristate | 1.86 ± 0.17 (57)$^b$ | 2.35 ± 0.24 (100) | 3.89 ± 0.47 (100) |
| n-octyl myristate | 2.28 ± 0.27 (70) | 1.55 ± 0.16 (66) | 2.73 ± 0.30 (70) |
| n-dodecyl myristate | 1.16 ± 0.11 (35) | 0.66 ± 0.07 (28) | 1.79 ± 0.20 (46) |
| n-hexadecyl myristate | 2.33 ± 0.22 (72) | 1.04 ± 0.08 (44) | 1.13 ± 0.13 (29) |
| n-octadecyl myristate | 3.26 ± 0.33 (100) | 1.71 ± 0.11 (72) | 1.19 ± 0.07 (31) |

$^a$Initial rate of reaction in the esterification of myristic acid with equimolar mixtures of different chain-length alkyl alcohols catalyzed by recombinant and a commercial CRLs.
$^b$The parentheses represent the ratio of the activity of each substrate to the highest one for the same enzyme.

TABLE 5

Esterfication of various chain-length acids with n-propanol.

| | LIP2 | LIP4 | CRL |
|---|---|---|---|
| | | ($10^3$ μmol/h/mg)[a] | |
| n-propyl butyrate | 9.96 ± 1.04 (100)[b] | 5.19 ± 0.49 (100) | 0.95 ± 0.05 (99) |
| n-propyl octanoate | 2.41 ± 0.24 (24) | 2.35 ± 0.11 (45) | 0.68 ± 0.05 (70) |
| n-propyl dodecanoate | 1.10 ± 0.13 (11) | 1.35 ± 0.06 (26) | 0.43 ± 0.05 (45) |
| n-propyl hexadecanoate | 0.68 ± 0.07 (7) | 1.56 ± 0.21 (30) | 0.96 ± 0.12 (100) |
| n-propyl octadecanoate | 0.77 ± 0.02 (8) | 1.01 ± 0.06 (19) | 0.94 ± 0.12 (98) |

[a]Initial rate of reaction in the esterification of n-propanol with equimolar mixtures of various chain-length fatty acids catalyzed by recombinant and commercial CRLs.
[b]The parentheses represent the ratio of the activity of each substrate to the highest one for the same enzyme.

Expression of Chimeric Proteins

Material and Methods

Construction of expression vectors The *E. coli* expression vectors pET23a-LIP4-S19 and pET23a-trx-LIP4-S19 were constructed as described in Tang et al. (2000) *Protein Exp. Purif.* 20: 308-313. Open-reading frames of LIP1, LIP2, LIP3, and LIP5 without the leader sequence were obtained by reverse transcription-polymerase chain reaction (RT-PCR). See Longhi et al. (1992) *Biochim. Biophy. Acta* 1131:227-232; and Lotti et al (1993) *Gene* 124:44-55. The chimeric DNA sequences were constructed by replacing the SphI (184)-BstXI (304) restriction DNA fragment of LIP4 with the corresponding fragments of LIP1, LIP2, LIP3, or LIP5, respectively. The resulting sequences encode mature chimeric *C. rugosa* lipases, denoted as TrX-LIP4/lid1, TrX-LIP4/lid2, TrX-LIP4/lid3, and TrX-LIP4/lid5, and were confirmed by DNA sequencing.

Preparation of recombinant LIP4 from *E. coli*. *E. coli* strain AD494 (DE3) (Novagen, Milwaukee, Wis.) harboring recombinant plasmid was grown overnight at 37° C. in Luria-Bertani (LB) broth supplemented with 50 μg/mL ampicillin and 15 μg/mL kanamycin. The cells were then diluted 20-fold into fresh medium and incubated with shaking at 25° C. After adding IPTG to give a final concentration of 0.05 mM, the cells were incubated at 10° C. until $OD_{600}$ reached 1.0.

Purification of recombinant LIP4. After induction, the AD494 (DE3) transformants were harvested by centrifugation at 4000 g and 4° C. for 10 min. The cell pellet was resuspended in TE buffer (20 mM Tris-HCl and 2.5 mM EDTA, pH 8.0). The cells were disrupted with a sonicator, and the soluble fractions of the cell lysates were then collected by centrifugation at 15,000 g at 4° C. for 30 min. The soluble fractions were concentrated by ultrafiltration on a 10,000 molecular weight cut-off membrane. These samples were then applied onto a DEAE-Sepharose CL-6B (Pharmacia Biotech) column equilibrated with TE buffer. Recombinant lipases were eluted using a linear gradient of 0 to 100 mM $(NH_4)_2SO_4$ over 5 column volumes.

The eluted proteins were then applied to a Butyl-Sepharose 4 Fast Flow (Pharmacia Biotech) hydrophobic interaction column. The column was washed with 5 bed volumes of TE buffer plus 1 mM and then 4 mM CHAPS. Bound proteins were then eluted with 5 bed volumes of TE buffer containing 30 mM CHAPS. The eluted samples were dialyzed against TE buffer and stored in a storage buffer (60 mM KCl, 10 mM Tris-HCl, 1.25 mM EDTA, 1% Triton X-100, and 17% glycerol, pH 7.5) at −20° C. Protein concentrations in the fractions were measured with the Bio-Rad assay kit, and esterase activity was determined using p-nitrophenyl butyrate as a substrate. The molecular masses of the purified recombinant lipases and a commercial lipase (Lipase Type VII, Sigma L1754) were determined by SDS-PAGE analysis.

Chimeric protein expression. A chimeric protein, its substrate interacting domain exchanged with one of another isomer, was prepared as described above.

Enzyme assay. Lipase activities were measured by titrimetry using tributyrin as substrates. The release of free fatty acid was continuously monitored by titration with 10 mM NaOH on the pH-Stat. The esterase activity at 37° C. was determined spectrophotometrically using p-nitrophenyl esters as substrates. One unit of activity was defined as the amount of enzyme that is able to release 1 μmol of p-nitrophenol per minute.

Results

To improve the protein solubility and facilitate the purification, the *E. coli* thioredoxin (Trx) was fused to the N-terminal of LIP4 to produce fusion protein Trx-LIP4. The Trx-LIP4 had better solubility and retained activity similar to native LIP4. Although the pairwise identities of overall amino acid sequence of LIP1, LIP2, LIP3 and LIP5, compared with LIP4, were 81, 83, 84 and 78%, respectively, but the substrate interacting domain (i.e., lid region) amino acid identities were 50, 53, 50 and 56% (Table 6), respectively.

To study the effect of the lid region on lipase activity and specificity, lid regions from the other four *C. rugosa* isoforms (LIP1, 2, 3, and 5; and corresponding lids 1, 2, 3, and 5) were exchanged with that of LIP4 and expressed as chimeric proteins Trx-LIP4/lid1, Trx-LIP4/lid2, Trx-LIP4/lid3 and Trx-LIP4/lid5, respectively. As shown in Table 7, the lipase hydrolysis activities of Trx-LIP4/lid2 and Trx-LIP4/lid3 increased 14% and 32%, respectively, whereas Trx-LIP4/lid1 and Trx-LIP4/lid5 decreased 85% and 20%, respectively, compared with native LIP4 with tributyrin as a substrate.

The effect of lid on lipase specificity depended greatly on which substrate was used. As shown in Table 8, although all the chimeric proteins with lid changes showed decreases in activity to varying extents, compared with native Trx-LIP4, the relative activities for various cholesterol esters of different chain length fatty acids showed substantial changes. For example, the best substrate for Trx-LIP4, Trx-LIP4/lid2 and Trx-LIP4/lid3 is cholesterol caprate, but the best for Trx-LIP4/lid1 and Trx-LIP4/lid5 is cholesterol stearate. In contrast, when p-nitrophenyl esters were used as substrates, both p-nitrophenyl caprate and stearate were the best substrates for Trx-LIP4 and Trx-LIP2, whereas only p-nitrophenyl caprate was the best substrate for Trx-LIP4/lid1, Trx-LIP4/lid3 and Trx-LIP4/lid5. The lid change also affected the substrate specificity of enzymes on the selectivity of cholesterol esters of various desaturated fatty acids. As shown in Table 9, the cholesteryl oleate (18:1) was the best substrate for Trx-LIP4, followed by cholesteryl linoleate (18:2, relative activity 68%), whereas cholesteryl stearate (18:0) was a poor substrate (relative activity 7%). Trx-LIP4/lid2 and Trx-LIP4/lid3 had a similar substrate preference pattern.

Further, the best substrate for Trx-LIP4/lid1 was cholesteryl stearate, followed by cholesteryl linoleate and then cholesteryl oleate. For Trx-LIP4/lid5, the substrate preference order was cholesteryl oleate, cholesteryl stearate, and cholesteryl linoleate. The kinetic parameters of various recombinant LIP4 chimeric proteins with cholesteryl linoleate were analyzed. As shown in Table 10, the fusion protein Trx-LIP4 showed a kcat/Km similar to native LIP4 although both Vmax and Km were increased. Trx-LIP4/lid2 retained a catalytic efficiency similar to Trx-LIP4, whereas Trx-LIP4/lid1, Trx-LIP4/lid3 and Trx-LIP4/lid5 showed greatly decreased kcat/Km. The decrease in the catalytic efficiency appeared due to the great decrease in kcat.

The lid domain also affected the enantioselectivity of lipase. As shown in Table 11, the C. rugosa lipase favored the hydrolysis of l-menthyl acetate over d-menthyl acetate. The recombinant Trx-LIP4 and all the chimeric LIP4 showed much better enantioselectivities than a commercial C. rugosa lipase (Lipase Type VII, Sigma). Only the enantioselectivity of Trx-LIP4/lid3 was similar to Trx-LIP4. Other chimeric proteins (Trx-LIP4/lid1, Trx-LIP4/lid2 and Trx-LIP4/lid5) showed substantial decreases in enantioselectivity with methyl acetate as a substrate. The enantioselectivity preference order might quite possibly change if other chiral substrates were used.

What is the structural basis of the lid domain effect on lipase catalysis? From computer analysis, positively charged Lys75 in the lid domain of native LIP4 (lid4) formed a hydrogen bonding and an electrostatic interaction with negatively charged Asp292, residing on the protein surface, to stabilize the lid4 in the open form conformation (an active state of lipase for hydrophobic substrates). Therefore this contributed to the high activity of LIP4 toward hydrophobic substrates such as medium and long chain fatty acid esters (Table 8-10). The lid2 domain has a lid conformation and amino acid residues similar to the lid4 in stabilizing the open form conformation (Table 6), and therefore the Trx-LIP4/lid2 chimeric protein showed a catalytic efficiency close to that of Trx-LIP4. In contrast, the Lys75-Asp292 interactions were disturbed by Glu71 in lid1, 3, and 5, and therefore these chimeric proteins showed great decreases in catalytic efficiency for hydrophobic substrates.

For short chain hydrophilic substrates, the effect of this open form stabilization is less important. Thus, the even better lipase activity of Trx-LIP4/lid3 for tributyrin hydrolysis than Trx-LIP4 (Table 7) might be due to the different conformations of active sites or substrate binding sites. Likewise, Trx-LIP4/lid3 showed a similar enantioselectivity to Trx-LIP4 (Table 11), and might assumed a similar catalytic machinery setting the chiral enantiopreference toward second alcohols. See Cygler et al. (1994) *J. Am. Chem. Soc.* 116: 3180-3186. In these cases, the effect of lid domain exchange could have been due to conformational changes, which had a subtle effect on the active site region and led to changes in substrate specificity and catalytic efficiency.

In conclusion, the lid domain has a significant effect on recombinant LIP enzyme catalytic efficiency, on the fatty acid chain length and desaturation selectivity of ester substrates, and on enantioselectivity. Therefore, the lid domain is a good choice for protein engineering to rationally design the biocatalytic properties of C. rugosa lipase for desired industrial applications. Site-directed mutagenesis on the lid region of LIP4 is currently underway to pinpoint the amino acid residues responsible for the substrate specificity, catalytic efficiency, enantioselectivity, and possibly enzyme stability.

TABLE 6

Comparison of overall and lid domain amino acid sequence identity of five C. rugosa lipase isoforms. Sequences were aligned by the CLUSTAL W program.

Pairwise identity (similarity) percentage of the full-length LIP proteins (534 aa).

|      | LIP1 | LIP2 | LIP3 | LIP4 | LIP5 |
| --- | --- | --- | --- | --- | --- |
| LIP1 | 100 (100) | 80 (89) | 88 (95) | 81 (90) | 82 (92) |
| LIP2 |      | 100 (100) | 82 (89) | 83 (91) | 77 (88) |
| LIP3 |      |      | 100 (100) | 84 (91) | 86 (94) |
| LIP4 |      |      |      | 100 (100) | 78 (90) |
| LIP5 |      |      |      |      | 100 (100) |

Among five sequences: identity = 66%; similarity = 81%.

Pairwise identity (similarity) percentage of the changed lid domains (redidue 63-94) of the wild type and chimeric LIP4.

|      | lid1 | lid2 | lid3 | lid4 | lid5 |
| --- | --- | --- | --- | --- | --- |
| lid1 | 100 (100) | 56 (75) | 81 (91) | 50 (72) | 88 (91) |
| lid2 |      | 100 (100) | 63 (78) | 53 (81) | 66 (81) |
| lid3 |      |      | 100 (100) | 50 (75) | 88 (94) |
| lid4 |      |      |      | 100 (100) | 56 (75) |
| lid5 |      |      |      |      | 100 (100) |

Among five sequences: identity = 37.5%; similarity = 62.5%.

TABLE 7

Lipase activity of recombinant LIP4 expressed in E. coli

| Enzyme | Specific activity ($10^3$ U/mg)[a] | Relative activity (%)[b] |
| --- | --- | --- |
| Trx-LIP4 | 6.76 | 100.0 |
| Trx-LIP4/lid1 | 1.03 | 15.2 |
| Trx-LIP4/lid2 | 7.71 | 114.2 |
| Trx-LIP4/lid3 | 8.90 | 131.7 |
| Trx-LIP4/lid5 | 5.37 | 79.5 |

[a]One lipase unit (U) is defined as the enzyme amount which produces 1.0 micromole of butyric acid from tributyrin per min at pH 7.0 and 37° C.
[b]Relative activity is the ratio of the activity of each enzyme to that of the wild type LIP4.

TABLE 8

Hydrolysis of cholesterol esters and p-nitrophenyl esters of various chain-length fatty acids.

| Enzyme | Cholesterol esterase activity ($10^{-2}$ U/mg)[a] | | | p-Nitrophenol esterase activity (U/mg)[a] | | |
|---|---|---|---|---|---|---|
|  | butyrate | caprate | stearate | butyrate | caprate | stearate |
| Trx-LIP4 | 6.2 (10)[b] | 62.2 (100) | 24.9 (40) | 12.5 (44) | 28.5 (100) | 28.2 (99) |
| Trx-LIP4/lid1 | 0.0 (0) | 3.7 (78) | 4.8 (100) | 0.7 (17) | 5.1 (100) | 0.6 (11) |
| Trx-LIP4/lid2 | 4.4 (9) | 47.7 (100) | 22.4 (47) | 7.3 (26) | 27.9 (100) | 26.9 (97) |
| Trx-LIP4/lid3 | 0.8 (6) | 14.5 (100) | 8.9 (61) | 1.2 (6) | 18.6 (100) | 5.0 (27) |
| Trx-LIP4/lid5 | 0.8 (11) | 6.4 (89) | 7.3 (100) | 0.5 (5) | 9.4 (100) | 1.0 (11) |

[a] One unit of activity (U) is the amount of enzyme necessary to hydrolyze 1.0 micromole of cholesteryl ester or p-nitrophenol ester per min at 37° C. and pH 7.0.
[b] Parentheses represent the ratio of the activity of each substrate to the highest one for the same enzyme.

TABLE 9

Hydrolysis of cholesterol esters of various unsaturated fatty acids.

| Enzyme | Cholesterol esterase activity ($10^{-2}$ U/mg)[a] | | |
|---|---|---|---|
|  | cholesteryl stearate (18:0) | cholesteryl oleate (18:1) | cholesteryl linoleate (18:1) |
| Trx-LIP4 | 24.9 (7)[b] | 354.6 (100) | 242.0 (68) |
| Trx-LIP4/lid1 | 4.8 (100) | 1.5 (32) | 2.5 (53) |
| Trx-LIP4/lid2 | 22.4 (9) | 244.7 (100) | 148.9 (61) |
| Trx-LIP4/lid3 | 8.9 (43) | 20.7 (100) | 18.6 (90) |
| Trx-LIP4/lid5 | 7.3 (85) | 8.5 (100) | 6.5 (76) |

[a] One unit of activity (U) is defined as the amount of enzyme necessary to hydrolyze 1.0 micromole of cholesteryl linoleate per minute at 37° C. and pH 7.0.
[b] The parentheses represent the ratio of the activity of each substrate to the highest one for the same enzyme.

TABLE 10

Kinetic parameters of a hydrolysis reaction using cholesteryl linoleate as the substrate.

| Enzyme | $M_r$ | $V_{max}$ $10^{-3}$ μmol/min/mg | $K_m$ $10^{-3}$ mM | $k_{cat}$ min$^{-1}$ | $k_{cat}/K_m$ mM$^{-1}$ min$^{-1}$ |
|---|---|---|---|---|---|
| Trx-LIP4 | 69680 | 2895 ± 117 | 104 ± 10 | 202 ± 8.12 | 1940 ± 139 |
| LIP4 | 57051 | 1235 ± 32 | 41 ± 5 | 70 ± 0.17 | 1740 ± 298 |
| Trx-LIP4/lid1 | 69717 | 28 ± 1 | 103 ± 5 | 2 ± 0.04 | 19 ± 0.47 |
| Trx-LIP4/lid2 | 69877 | 1851 ± 24 | 74 ± 3 | 129 ± 0.22 | 1751 ± 64 |
| Trx-LIP4/lid3 | 69757 | 231 ± 14 | 46 ± 1 | 16 ± 0.17 | 349 ± 7 |
| Trx-LIP4/lid5 | 69797 | 70 ± 4.8 | 34 ± 1 | 5 ± 0.01 | 147 ± 3 | a. The assay temperature was 37° C. and pH was 7.0. The concentrations of Trx-LIP4, LIP4, Trx-LIP4/lid1, Trx-LIP4/lid2, Trx-LIP4/lid3 and Trx-LIP4/lid5 were 29 nM, 39 nM, 11 nM, 86 nM, 58 nM and 66 nM, respectively. The values are averages from three independent experiments.

b. The molecular weights of recombinant proteins were predicted from the deduced amino acid sequences and those of commercial enzymes were determined from SDS-PAGE.

TABLE 11

The enantioselectivity of recombinant LIP4s expressed in E. coli and a commercial lipase (CRL) with (d)- and (l)-menthyl acetate as substraes.

| Enzyme | v(l)[a] (umol/h/mg) | v(d) (umol/h/mg) | Enantioselectivity[b] v(l)/v(d) |
|---|---|---|---|
| Trx-LIP4 | 53.65 ± 4.10 | 1.69 ± 0.13 | 31.73 |
| Trx-LIP4/lid1 | 2.15 ± 0.18 | 0.40 ± 0.06 | 5.35 |
| Trx-LIP4/lid2 | 33.00 ± 3.48 | 2.89 ± 0.45 | 11.41 |
| Trx-LIP4/lid3 | 54.11 ± 3.10 | 1.70 ± 0.23 | 31.81 |
| Trx-LIP4/lid5 | 6.02 ± 0.57 | 0.48 ± 0.06 | 12.59 |
| CRL | 53.58 ± 3.38 | 42.65 ± 7.67 | 1.26 |

[a]Specific activity (v) is defined as the amount of (d)- or (l)-menthol released per mg of enzyme per hour at 30° C. and pH 7.0.

OTHER EMBODIMENTS

All of the features disclosed in this specification may be combined in any combination. Each feature disclosed in this specification may be replace by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

---

What is claimed is:

1. An isolated nucleic acid comprising a DNA that encodes, in a non-*Candida rugosa* cell, a lipase at least 98% identical to SEQ ID NO:2, wherein the DNA has at least 15 CTG codons encoding the serines in SEQ ID NO:2, when expressed in *Candida rugosa*, replaced with a universal serine codon selected from TCT, TCC, TCA, TCG, AGT, or AGC.

2. The nucleic acid of claim 1, wherein the DNA has all of the CTG codons encoding the serines in SEQ ID NO:2, when expressed in *Candida rugosa*, replaced with a universal serine codon selected from TCT, TCC, TCA, TCG, AGT, or AGC.

3. The nucleic acid of claim 2, wherein the DNA encodes, in a non-*Candida rugosa* cell, SEQ ID NO:2.

4. The nucleic acid of claim 1, wherein the DNA consists of the nucleotide sequence of SEQ ID NO:1 or a degenerative variant thereof.

5. A microorganism comprising the nucleic acid of claim 1, wherein the microorganism is a bacterium or a yeast.

6. The microorganism of claim 5, wherein the bacterium is *E. coli* and the yeast is *P. pastoris*.

7. The microorganism of claim 5, wherein the nucleic acid encodes, in a non-*Candida rugosa* cell, the lipase set forth by SEQ ID NO:2.

8. The microorganism of claim 7, wherein the bacterium is *E. coli*. and the yeast is *P. pastoris*.

9. The microorganism of claim 5, wherein the DNA comprising the nucleotide sequence of SEQ ID NO:1 or a degenerative variant thereof.

10. The microorganism of claim 9, wherein the bacterium is *E. coli*. and the yeast is *P. pastoris*.

11. An isolated nucleic acid comprising the DNA of SEQ ID NO:1 or a degenerate variant thereof.

* * * * *